US006589665B2

(12) United States Patent
Chabrecek et al.

(10) Patent No.: US 6,589,665 B2
(45) Date of Patent: Jul. 8, 2003

(54) COATED ARTICLES

(75) Inventors: Peter Chabrecek, Riehen (CH); Dieter Lohmann, Münchenstein (CH); Jörg Leukel, Freiburg (DE); Lynn Cook Winterton, Alpharetta, GA (US); Yongxing Qiu, Dunwoody, GA (US); John Martin Lally, Lilburn, GA (US)

(73) Assignee: Novartis AG, Basel (CH)

( * ) Notice: Subject to any disclaimer, the term of this patent is extended or adjusted under 35 U.S.C. 154(b) by 89 days.

(21) Appl. No.: 09/867,827

(22) Filed: May 30, 2001

(65) Prior Publication Data

US 2002/0006493 A1 Jan. 17, 2002

Related U.S. Application Data

(60) Provisional application No. 60/228,022, filed on Aug. 24, 2000.

(30) Foreign Application Priority Data

May 30, 2000 (EP) ............................................. 00111526

(51) Int. Cl.$^7$ .............................. G02B 1/04; B32B 27/30
(52) U.S. Cl. ....................... 428/520; 427/2.24; 427/508; 428/500; 428/515; 428/522
(58) Field of Search ................................ 428/500, 515, 428/520, 522; 427/2.24, 508

(56) References Cited

U.S. PATENT DOCUMENTS 5,807,636 A    9/1998    Sheu et al. ................. 428/403
5,837,636 A    11/1998   Sechrist et al. ............... 502/35

FOREIGN PATENT DOCUMENTS

| EP | 1 095 711 A | 10/2000 |
|---|---|---|
| EP | 1 095 966 A | 10/2000 |
| WO | WO 96/20796 | 7/1996 |
| WO | WO 96/20919 | 7/1996 |
| WO | WO 99/35520 | 7/1999 |
| WO | WO 99/57581 | 11/1999 |

OTHER PUBLICATIONS

European Search Report Date: Nov. 2, 2000.

*Primary Examiner*—D. S. Nakarani
(74) *Attorney, Agent, or Firm*—Jian S. Zhou; Richard I Gearhart; R. Scott Meece

(57) ABSTRACT

The invention relates to novel composite materials comprising
(a) an inorganic or organic bulk material having attached to its surface at least one polyionic material that comprises covalently bound initiator moieties for radical polymerization; and
(b) a hydrophilic surface coating obtainable by applying one or more different ethylenically unsaturated hydrophilic monomers or macromonomers to the bulk material surface provided with the initiator radicals and polymerizing said monomers or macromonomers.

The composite materials of the invention have desirable characteristics regarding adherence to the substrate, durability, hydrophilicity, wettability, biocompatibility and permeability and are thus useful for the manufacture of biomedical articles such as ophthalmic devices.

26 Claims, No Drawings

COATED ARTICLES

This application claims benefit of provisional application 60/228,022 filed Aug. 24, 2000.

The present invention relates to coated articles such as biomedical articles, especially contact lenses, which are at least partly coated with a hydrophilic polymer, and to a process for the manufacture of said coated articles.

A variety of different types of processes for preparing hydrophilic polymeric coatings on an "inert" hydrophobic substrate have been disclosed in the prior art. For example, WO 99/57581 discloses to first of all provide the article surface with covalently bound photoinitiator molecules, coating the modified surface with a layer of a polymerizable macromonomer and then subjecting it to a heat or radiation treatment whereby the macromonomer is graft polymerized thus forming the novel article surface. The covalent binding of the photoinitiator molecules to the article surface is created by first subjecting the article surface to a plasma treatment thereby providing the surface with functional groups, and then reacting said functional groups with core-active groups of a functional photoinitiator.

A plasma treatment requires a considerable investment in equipment and is furthermore difficult to be integrated in an automated production process. For example, a plasma treatment requires that the article to be treated is dry before exposure to the plasma. Thus, a polymeric article such as a contact lens that is wet from prior hydration or extraction must be dried previously, thereby adding time in the overall lens production process as well as imposing added costs of obtaining a drying equipment.

Therefore, it would be highly desirable to modify the surface functionalization step of the process disclosed in WO 99/57581 such that the plasma treatment is avoided and replaced by a technique which is easy to perform with standard equipment and which is thus more feasible for an automated production process.

Surprisingly, it has now been found, that hydrophobic articles may be readily functionalized by adding at least one polyelectrolyte or preferably a bilayer of functional polyelectrolytes to the article surface. The functional groups of the polyelectrolytes that are adsorbed and/or heteropolarly bound on the surface then may be used for the covalent attachment of polymerization initiators which in turn may initiate the graft polymerization of suitable hydrophilic monomers or macromonomers onto the article surface.

The present invention therefore in one aspect relates to a composite material comprising (a) an inorganic or organic bulk material having attached to its surface a polyionic material that comprises covalently bound initiator moieties for radical polymerization; and (b) a hydrophilic surface coating obtainable by applying one or more different ethylenically unsaturated hydrophilic monomers or macromonomers to the bulk material surface provided with the initiator radicals and polymerizing said monomers or macromonomers.

The bulk material underlying the composite materials of the invention is preferably a material that is devoid of ionic groups such as cationic or anionic groups. Accordingly, the surface of the preferred bulk materials is also devoid of ionic groups such as carboxy, sulfo, amino and the like groups and is thus substantially free from ionic charges.

Examples of suitable bulk materials are quartz, ceramics, glasses, silicate minerals, silica gels, metals, metal oxides, carbon materials such as graphite or glassy carbon, natural or synthetic organic polymers, or laminates, composites or blends of said materials, in particular natural or synthetic organic polymers or modified biopolymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polyacrylamides, polymethacrylamides, polystyrene, polyethylene and halogenated derivatives thereof, polyvinyl acetate and polyacrylonitrile); or elastomers (silicones, polybutadiene and polyisoprene).

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene or propylene, for example tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred materials to be coated are amphiphilic segmented copolymers comprising at least one hydrophobic segment and at least one hydrophilic segment which are linked through a bond or a bridge member. Examples are silicone hydrogels, for example those disclosed in PCT applications WO 96/31792 and WO 97/49740 which are herewith incorporated by reference.

A particular preferred group of bulk materials comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or Silastic™ type polymer, or a composite made therefrom.

Moreover, the material to be coated may also be an inorganic or metallic base material without suitable reactive groups, e.g. ceramic, quartz, or metals, such as silicon or gold, or other polymeric or non-polymeric substrates. E.g. for implantable biomedical applications, ceramics are very useful. In addition, e.g. for biosensor purposes, hydrophilically coated base materials are expected to reduce nonspecific binding effects if the structure of the coating is well controlled. Biosensors may require a specific carbohydrate coating on gold, quartz, or other non-polymeric substrates.

The form of the material to be coated may vary within wide limits. Examples are particles, granules, capsules, fibres, tubes, films or membranes, preferably moldings of all kinds such as ophthalmic moldings, for example intraocular lenses, artificial cornea or in particular contact lenses.

The polyionic material being attached to the bulk material surface may consist of one single ionic polymer, for example of a polyanionic or polycationic material as described below.

Preferably, the polyionic material includes at least one bilayer, the bilayer comprising a first ionic polymer and a second ionic polymer having charges opposite of the charges of the first ionic polymer.

A suitable bilayer on the bulk material comprises a first and second ionic polymer having opposite charges, wherein "first ionic polymer" indicates the polymer that is first of all applied to the article surface, and "second ionic polymer" indicates the polymer that is applied to the article surface after it has already been modified with the first ionic polymer. The bulk material may comprise one or more than one bilayers, for example from 1 to 25 bilayers containing the same or different ionic polymers in each case, preferably from 1 to 20 bilayers, more preferably 1 to 10 bilayers, even more prefereably 1 to 5 bilayers and in particular just one bilayer.

The first ionic polymer may be cationic or anionic, preferably anionic. A suitable anionic polymer is, for example, a synthetic polymer, biopolymer or modified biopolymer comprising carboxy, sulfo, sulfato, phosphono or phosphato groups or a mixture thereof, or a salt thereof, for example a biomedical acceptable salt and especially an ophthalmically acceptable salt thereof. Anionic polymers comprising carboxy groups or a suitable salt thereof are preferred.

Examples of synthetic anionic polymers are: a linear polyacrylic acid (PAA), a branched polyacrylic acid, for example a Carbophile or Carbopol® type from Goodrich Corp., a polymethacrylic acid (PMA), a polyacrylic acid or polymethacrylic acid copolymer, for example a copolymer of acrylic or methacrylic acid and a further vinylmonomer, for example acrylamide, N,N-dimethyl acrylamide or N-vinylpyrrolidone, a maleic or fumaric acid copolymer, a poly(styrenesulfonic acid) (PSS), a polyamido acid, for example a carboxy-terminated polymer of a diamine and a di- or polycarboxylic acid, for example carboxy-terminated Starburst™ PAMAM dendrimers (Aldrich), a poly(2-acrylamido-2-methylpropanesulfonic acid) (poly-(AMPS)), or an alkylene polyphosphate, alkylene polyphosphonate, carbohydrate polyphosphate or carbohydrate polyphosphonate, for example a teichoic acid.

Examples of anionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextranes, alginates, pectins, gellan, carboxyalkyl chitins, carboxymethyl chitosans, sulfated polysaccharides.

A preferred anionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable cationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents. Cationic polymers comprising primary or secondary amino groups or a salt thereof are preferred.

Examples of synthetic cationic polymers are:

(i) a polyallylamine (PAH) homo- or copolymer, optionally comprising modifier units;

(ii) a polyethyleneimine (PEI);

(iii) a polyvinylamine homo- or copolymer, optionally comprising modifier units;

(iv) a poly(vinylbenzyl-tri-$C_1$–$C_4$-alkylammonium salt), for example a poly(vinylbenzyl-tri-methyl ammoniumchloride);

(v) a polymer of an aliphatic or araliphatic dihalide and an aliphatic N,N,N',N'-tetra-$C_1$–$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;

(vi) a poly(vinylpyridin) or poly(vinylpyridinium salt) homo- or copolymer;

(vii) a poly (N,N-diallyl-N,N-di-$C_1$–$C_4$-alkyl-ammoniumhalide) comprising units of formula

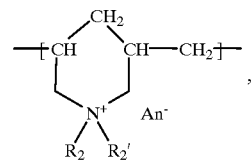

wherein $R_2$ and $R_2'$ are each independently $C_1$–$C_4$-alkyl, in particular methyl, and An⁻ is a, for example, a halide anion such as the chloride anion;

(viii) a homo- or copolymer of a quaternized di-$C_1$–$C_4$-alkyl-aminoethyl acrylate or methacrylate, for example a poly(2-hydroxy-3-methacryloylpropyltri-$C_1$–$C_2$-alkylammonium salt) homopolymer such as a a poly (2-hydroxy-3-methacryloylpropyltri-methylammonium chloride), or a quaternized poly(2-dimethylaminoethyl methacrylate or a quaternized poly (vinylpyrrolidone-co-2-dimethylaminoethyl methacrylate);

(ix) POLYQUAD® as disclosed in EP-A-456,467; or (x) a polyaminoamide (PAMAM), for example a linear PAMAM or a PAMAM dendrimer such as a amino-terminated Starbust™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, acrylamide, methacrylamide, N,N-dimethyl acrylamide, N-vinylpyrrolidone and the like.

Suitable modifier units of the polyallylamine (i) are, for example, of formula

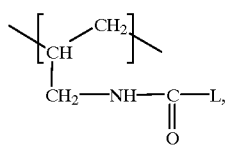

(5)

wherein L is $C_2$–$C_6$-alkyl which is substituted by two or more same or different substituents selected from the group consisting of hydroxy, $C_2$–$C_5$-alkanoyloxy and $C_2$–$C_5$-alkylaminocarbonyloxy.

L is preferably linear $C_3$–$C_6$-alkyl, more preferably linear $C_4$–$C_5$-alkyl, and most preferably n-pentyl which is in each case substituted as defined above.

Suitable substituents of the alkyl radical L are —OH, a radical —O—C(O)—$R_{29}$ and/or a radical —O—C(O)—NH—$R_{29}$, wherein $R_{29}$ and $R_{29}'$ are each independently of the other $C_1$–$C_4$-alkyl, preferably methyl, ethyl or n- or iso-propyl, and more preferably methyl or ethyl.

Preferred substituents of the alkyl radical L are hydroxy, acetyloxy, propionyloxy, methyl-aminocarbonyloxy or ethylaminocarbonyloxy, especially hydroxy, acetyloxy or propionyloxy and in particular hydroxy.

A preferred embodiment relates to polyallyl amines comprising units of the above formula (5), wherein L is a radical of formula

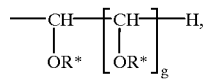

(6)

wherein g is 1, 2, 3, 4 or 5, preferably 3 or 4 and in particular 4, each R* is independently hydrogen or a radical —C(O)—$R_{29}$ or —C(O)—NH—$R_{29}'$, and for $R_{29}$ and $R_{29}'$ the above meanings and preferences apply. L is even more preferred a radical of the above formula (6) wherein g is 3 or 4, in particular 4, and each group —OR* independently is hydroxy or hydroxy which is partly or completely acetylated, in particular hydroxy. Particular preferred radicals L are 1,2,3,4,5-pentahydroxy-n-pentyl or 1,2,3,4,5-pentahydroxy-n-pentyl wherein the hydroxy groups are partly or completely acetylated.

The modified polyallylamines of the invention are derivatives of a polyallyl amine that, based on the number of amino groups of the polyallyl amine, comprise from about 1 to 99%, preferably from 10 to 80%, more preferably, from 15 to 75%, even more preferably 20 to 70% and in particular 40 to 60%, of units of formula (5).

The term units of formula (5) or of another formula number below is always to be understood as encompassing one or more different species failing under the respective formula. Preferably the term means one single species. In addition, the polyallylamine may contain further modifier units, for example those disclosed in EP-A-1002807, formula (2a)-(2d).

A preferred polyallylamine according to the invention is a polyallylamine without modifier units or a polyallylamine having from 10 to 80% of units of the above formula (5) based on the number of amino groups of the polyallyl amine. A particular preferred polyallylamine according to the invention is a polyallylamine without modifier units or a polyallylamine having from 15 to 75%, based on the number of amino groups of the polyallyl amine, of units of the above formula (5) wherein L is 1,2,3,4,5-pentahydroxy-n-pentyl.

Suitable modifier units of the polyvinylamine (iii) are, for example, of formula

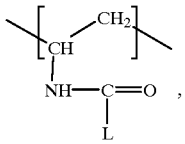

(5a)

wherein for L the above-given meanings and preferences apply.

A suitable polyvinylamine copolymer is, for example, a copolymer comprising vinylamine units and units derived from another hydrophilic comonomer, for example from acrylamide, N,N-dimethyl acrylamide, N-vinylpyrrolidone or the like.

Examples of cationic biopolymers or modified biopolymers are: basic peptides, proteins or glucoproteins, for example a poly-s-lysine, albumin or collagen, aminoalkylated polysaccharides, for example a chitosan, aminodextranes.

A preferred cationic polymer forming the bilayer that is attached to the bulk material is a polyallylamine homopolymer; a polyallylamine comprising modifier units of the above formula (1); a polyvinylamine homo- or -copolymer or a polyethyleneimine homopolymer, in particular a polyallylamine or polyethyleneimine homopolymer or a poly(vinylamine-co-acrylamid) copolymer.

The molecular weight of the anionic and cationic polymers used to prepare the bilayers may vary within wide limits depending on the desired characteristics such as adhesion on the bulk material, coating thickness and the like. In general, a weight average molecular weight of from about 5000 to about 5000000, preferably from 10000 to 1000000, more preferably 15000 to 500000, even more preferably from 20000 to 200000 and in particular from 40000 to 150000, has proven as valuable both for the anionic and cationic polymer forming the bilayer.

The anionic and cationic polymers used to prepare the bilayers are in general water-soluble. The anionic and cationic polymers forming the bilayers of the invention are known and the majority of them is commercially available, or they may be prepared according to methods known in the art. Polyallylamines comprising modifier units are known, for example, from EP-A-1002807.

The formation and application of the bilayers on the bulk material surface may be accomplished according to processes known per se. For example, the bulk material is immersed in a solution of the anionic and cationic polymer, or one or more layers each of the anionic and cationic polymer are successively deposited on the modified bulk material surface, for example, by dipping, spraying, printing, spreading, pouring, rolling, spin coating or vacuum vapor deposition, spraying or particularly dipping being preferred. Following the deposition of one ionic polymer the bulk material may be rinsed or dried before the deposition of the next ionic polymer having opposite charges. However, it is preferred to omit a rinsing or drying step between the attachment of the first and second ionic polymer.

A preferred dip method involves the steps of (i) applying a coating of a first ionic polymer, for example of a cationic or preferably of an anionic polymer, to the bulk material by immersing the bulk material in a solution of the first ionic polymer; (ii) optionally, rinsing the bulk material by immersing it in a rinsing solution; (iii) optionally, drying said bulk material; and (iv) applying a coating of a second ionic polymer having charges opposite of the charges of the first ionic polymer, for example an anionic or preferably a cationic polymer, to the bulk material by immersing the bulk material in a solution of the second ionic polymer. A more preferred dip method involves the steps of applying a coating of the first and second ionic polymer by immersing the bulk material successively in a solution each of the first and second ionic polymer without a rinsing or drying step in between. A further dip method involves immersing the bulk material in a solution comprising both the anionic and cationic polymer.

The dip solutions of the anionic and cationic polymer in general comprise the respective polymer diluted in one or more different solvents. Suitable solvents are, for example, water or an aqueous solution comprising a water-miscible organic solvent, for example a $C_1$–$C_4$-alkanol such as methanol or ethanol; the preferred solvent is pure water. The aqueous solutions of the cationic or anionic polymer advantageously each have a slightly acidic pH value, for example a pH from about 2 to about 5 and preferably from about 2.5 to about 4.5. The concentration of the dip solutions may vary within wide limits depending, for example, on the particular ionic polymer involved. However, it is generally preferred to formulate relatively dilute solutions of the ionic polymers. A preferred anionic or cationic polymer concentration is from about 0.0001 to about 0.25 weight percent, more preferably from 0.0005 to 0.15 weight percent and in particular from 0.001 to 0.1 percent by weight, relative to the total weight of the solution.

A suitable rinsing solution, if used, is preferably an aqueous solution, in particular an aqueous solution buffered at a pH of about 2 to about 7, more preferably from 2 to 5 and even more preferably from 2.5 to 4.5.

Partial drying or removal of excess rinsing solution from the surface between solution applications, if applicable, may be accomplished by a number of means known in the art. While the bulk material may be partially dried by merely allowing the lens to remain in an air atmosphere for a certain period of time, it is preferable to accelerate the drying by application of a mild stream of air to the surface. The flow rate may be adjusted as a function of the strength of the material being dried and the mechanical fixturing of the material. It should be noted that there is no requirement to completely dry the bulk material. The "partial drying" step, as used herein, refers to a removal of droplets of solution which cling to the lens surface, rather than a desiccation of the lens. Thus, it is preferred to dry only to the extent that any water or solution film on the surface is removed.

The thickness of the coating may be adjusted by addition of one or more salts, such as sodium chloride, to the ionic polymer solution. A preferred salt concentration is about 0.1 to about 2.0 weight percent. As the salt concentration is increased, the polyelectrolyte takes on a more globular conformation. However, if the concentration is raised too high, the polyelectrolyte will not deposit well, if at all, on the lens surface. A more preferred salt concentration is about 0.7 to about 1.3 weight percent.

The bilayer formation process may be repeated a plurality of times, for example from 1 to 24 times, preferably from 1 to 14 times, more preferably from 1 to 9 times; according to one embodiment just one bilayer is deposited.

The immersion time for each of the coating and optional rinsing steps may vary depending on a number of factors. In general a rinsing time of from about 30 seconds to about 30 minutes, prefereably from 1 to 20 minutes, more preferably 1 to 10 minutes and in particular 1 to 6 minutes has proven as valuable. The immersion in the polymer solutions takes place, for example, at room temperature or at elevated temperature, preferably at room temperature, for example at a temperature of from 15 to 30° C. Following the dipping steps the bulk material may be subjected to a heat treatment in order to compact or stabilize the bilayer(s) on the bulk material surface.

Instead of coating the bulk material by means of a dip technique, said coating may also take place using spray coating techniques, wherein the above given conditions and features concerning solvents, concentrations, presence of salts, pH, temperature, number and sequence of coating steps, optional rinsing or drying steps apply accordingly. Spray coating technique in this context comprises any known process in the art including, for example, conventional techniques of applying a fluid, or techniques using ultrasonic energy, or electrostatic spray coating techniques. In addition a mixture of dip and spray techniques may also be employed.

In addition, if the polyionic material on the material surface consists of one single ionic polymer only, said ionic polymer may be applied to the surface as described above, in particular by dipping or spraying.

According to the above-mentioned methods bulk materials are obtained that comprise one polyelectrolyte or preferably one or more bilayers of polyelectrolytes adsorbed and/or heteropolarly bound on the surface. Due to this modification the surface is provided with functional groups, for example with carboxy, sulfone, sulfato, phosphono or phosphato groups or with primary, secondary or tertiary amine groups; said functional groups, preferably the carboxy groups or in particular the primary or secondary amino groups, may be further reacted with a functional initiator for radical polymerization.

Polymerization initiators bound to the polyionic material that is attached to the bulk material surface are typically those that are initiating a radical polymerization of ethylenically unsaturated compounds. The radical polymerization may be induced thermally, or preferably by irradiation.

Suitable thermal polymerization initiators are known to the skilled artisan and comprise for example peroxides, hydroperoxides, azo-bis(alkyl- or cycloalkylnitriles), persulfates, percarbonates or mixtures thereof. An example for a functionalized thermal initiator is 4,4'-azo-bis(4-cyanovaleric acid) or derivatives thereof.

Initiators for the radiation-induced polymerization are particularly functional photoinitiators having a photoinitiator part and in addition a functional group that is coreactive with functional groups of the bilayers, particularly with amino or carboxy groups. The photoinitiator part may belong to different types, for example to the thioxanthone type and preferably to the benzoin type. Suitable functional groups that are coreactive with the bilayers attached to the surface of the bulk material are for example a carboxy, hydroxy, epoxy or particularly an isocyanato group.

Preferred polymerization initiators for use in the present invention are the photoinitiators of formulae (I) and (Ia) as disclosed in U.S. Pat. No. 5,527,925, those of the formula (I) as disclosed in PCT application WO 96/20919, or those of formulae II and III including formulae IIa–IIy and IIIg as disclosed in EP-A-0281941, particularly formulae IIb, IIi, IIm, IIn, IIp, IIr, IIs, IIx and IIIg therein. The respective portion of said three documents including the definitions and preferences given for the variables in said formulae are herewith included by reference.

The polymerization initiator moieties are preferably derived from a functional photoinitiator of the formula

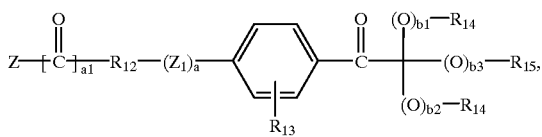 (10a)

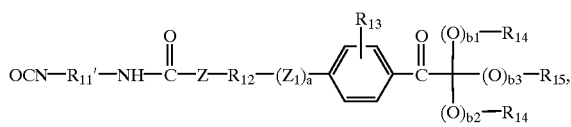 (10b)

or

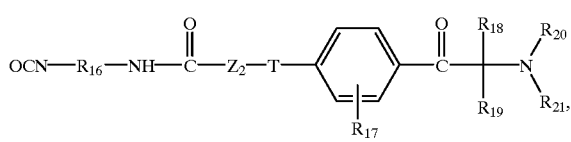 (10c)

wherein Z is bivalent —O—, —NH— or —NR$_{22}$—; Z$_1$ is —O—, —O—(O)C-, —C(O)—O— or —O—C(O)—O—; R$_{13}$ is H, C$_1$–C$_{12}$-alkyl, C$_1$–C$_{12}$-alkoxy or N-C$_1$–C$_{12}$-alkylamino; R$_{14}$ and R$_{15}$ are each independently of the other H, linear or branched C$_1$–C$_8$-alkyl, C$_1$–C$_8$-hydroxyalkyl or C$_6$–C$_{10}$-aryl, or the groups R$_{14}$—(O)$_{b1}$— and R$_{14}$—(O)$_{b2}$— together are —(CH$_2$)$_c$— wherein c is an integer from 3 to 5, or the groups R$_{14}$—(O)$_{b1}$—, R$_{14}$—(O)$_{b2}$— and R$_{15}$—(O)$_{b3}$— together are a radical of the formula

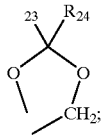

R$_{12}$ is a direct bond or linear or branched C$_1$–C$_8$-alkylene that is unsubstituted or substituted by —OH and/or is uninterrupted or interrupted by one or more groups —O—, —O—C(O)— or —O—C(O)—O—; R$_{11}$' is branched C$_3$–C$_{18}$-alkylene, unsubstituted or C$_1$–C$_4$-alkyl- or C$_1$–C$_4$-alkoxy-substituted C$_6$–C$_{10}$-arylene, or unsubstituted or C$_1$–C$_4$-alkyl- or C$_1$–C$_4$-alkoxy-substituted C$_7$–C$_{18}$-aralkylene unsubstituted or C$_1$–C$_4$-alkyl- or C$_1$–C$_4$-alkoxy-substituted C$_3$–C$_8$-cycloalkylene, unsubstituted or C$_1$–C$_4$-alkyl- or C$_1$–C$_4$-alkoxy-substituted C$_3$–C$_8$-cycloalkylene-C$_y$H$_{2y}$— or unsubstituted or C$_1$–C$_4$-alkyl- or C$_1$–C$_4$-alkoxy-substituted —C$_y$H$_{2y}$—(C$_3$–C$_8$-cycloalkylenee)-C$_y$H$_{2y}$— wherein y is an integer from 1 to 6; R$_{16}$ independently has the same definitions as R$_{11}$' or is linear C$_3$–C$_{18}$-alkylene; R$_{22}$ is linear or branched C$_1$–C$_6$-alkyl; T is bivalent —O—, —NH—, —S—, C$_1$–C$_8$-alkylene or 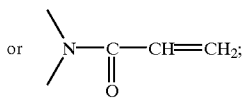

Z$_2$ is a direct bond or —O—(CH$_2$)$_d$— wherein d is an integer from 1 to 6 and the terminal CH$_2$ group of which is linked to the adjacent T in formula (10c); R$_{17}$ is H, C$_1$–C$_{12}$-alkyl, C$_1$–C$_{12}$-alkoxy, N-C$_1$–C$_{12}$-alkylamino or —NR$_2$,R$_{26}$ wherein R$_{25}$ is C$_1$–C$_8$-alkyl and R$_{26}$ is H or C$_1$–C$_8$-alkyl; R$_{18}$ is linear or branched C$_1$–C$_8$-alkyl, C$_2$–C$_8$-alkenyl or C$_6$–C$_{10}$-aryl-C$_1$–C$_8$-alkyl; R$_{19}$ independently of R$_{18}$ has the same definitions as R$_{18}$ or is C$_6$–C$_{10}$-aryl, or R$_{18}$ and R$_{19}$ together are —(CH$_2$)$_e$— wherein e is an integer from 2 to 6; R$_{20}$ and R$_{21}$ are each independently of the other linear or branched C$_1$–C$_8$-alkyl that may be substituted by C$_1$–C$_4$-alkoxy, or C$_6$–C$_{10}$-aryl-C$_1$–C$_8$-alkyl or C$_2$–C$_8$-alkenyl; or R$_{20}$ and R$_{21}$ together are —(CH$_2$)$_{11}$—Z$_3$—(CH$_2$)$_{f2}$— wherein Z$_3$ is a direct bond, —O—, —S— or —NR$_{26}$-, and R$_{26}$ is H or C$_1$–C$_8$-alkyl and f1 and f2 are each independently of the other an integer from 2 to 4; R$_{23}$ and R$_{24}$ are each independently of the other H, C$_1$–C$_8$-alkyl, C$_3$–C$_8$-cycloalkyl, benzyl or phenyl; and a, a1, b1, b2 and b3 are each independently of the other 0 or 1; subject to the provisos that b1 and b2 are each 0 when R$_{15}$ is H; that the total of (b1+b2+b3) is not exceeding 2; and that a is 0 when R$_{12}$ is a direct bond.

A preferred sub-group of compounds of formula (10a) or (10b) comprises those wherein, b1 and b2 are each 0; Z and Z$_1$ are each bivalent —O—; b3 is 0 or 1; R$_{14}$ is C$_1$–C$_4$-alkyl or phenyl, or both groups R$_{14}$ together are tetramethylene or pentamethylene; R$_{15}$ is C$_1$–C$_4$-alkyl or H, R$_{13}$ is hydrogen; a and a1 are each independently 0 or 1; R$_{12}$ is linear or branched C$_2$–C$_4$-alkylene, or is a direct bond, in which case a is 0; R$_{11}$' is branched C$_5$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-C$_y$H$_{2y}$— or —C$_y$H$_{2y}$-cyclohexyl-C$_y$H$_{2y}$— or cyclohexyl-C$_y$H$_{2y}$— or —C$_y$H$_{2y}$-cyclohexyl-C$_y$H$_{2y}$— substituted by from 1 to 3 methyl groups; y is 1 or 2; and R$_{16}$ has the same definitions as R$_{11}$, or is linear C$_3$–C$_{10}$alkylene.

An especially preferred sub-group of compounds of formula (10a) or (10b) comprises those wherein, b1 and b2 are each 0, Z and Z. are each bivalent —O—, b3 is 0 or 1; R$_{14}$ is methyl or phenyl, or both groups R$_{14}$ together are pentamethylene; R$_{15}$ is methyl or H; R$_{13}$ is hydrogen; a is 1 and R$_{12}$ is ethylene, or a is 0 and R$_{12}$ is a direct bond; a1 is 0 or 1; R$_{11}$' is branched C$_1$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-CH$_2$— or cyclohexyl-CH$_2$-substituted by from 1 to 3 methyl groups; R$_{16}$ has the same definitions as R$_{11}$ or is linear C$_5$–C$_{10}$alkylene.

A preferred sub-group of compounds of formula (10c) comprises those wherein T is bivalent —O—, —NH—, —S— or —(CH$_2$)$_y$— wherein y is an integer from 1 to 6; Z$_2$ is a direct bond or —O—(CH$_2$)$_y$— wherein y is an integer from 1 to 6 and the terminal CH$_2$ group of which is linked to the adjacent T in formula (10c); R$_{17}$ is H, C$_1$–C$_{12}$-alkyl or C$_1$–C$_{12}$-alkoxy; R$_{18}$ is linear C$_1$–C$_8$-alkyl, C$_2$–C$_8$-alkenyl or C$_6$–C$_{10}$-aryl-C$_1$–C$_8$-alkyl; R$_{19}$ independently of R$_{18}$ has the same definitions as R$_{18}$ or is C$_6$–C$_{10}$-aryl, or R$_{15}$ and R$_{19}$ together are —(CH$_2$)$_e$— wherein e is an integer from 2 to 6; R$_{20}$ and R$_{21}$ are each independently of the other linear or branched C$_1$–C$_8$-alkyl that may be substituted by C$_1$–C$_4$-alkoxy, or C$_6$–C$_{10}$-aryl-C$_1$–C$_8$-alkyl or C$_2$–C$_8$-alkenyl; or R$_{20}$ and R$_{21}$ together are —(CH$_2$)$_{f1}$—Z$_3$—(CH$_2$)$_{f2}$— wherein Z$_3$ is a direct bond, —O—, —S— or —NR$_{26}$—, and R$_{26}$ is H or C$_1$–C$_8$-alkyl and f1 and f2 are each independently of the other an integer from 2 to 4; and R$_{16}$ is branched C$_6$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-CH$_2$- or cyclohexylene-CH$_2$— substituted by from 1 to 3 methyl groups.

An especially preferred sub-group of compounds of formula (10c) comprises those wherein T is bivalent —O—; Z$_2$ is —O—(CH$_2$)$_y$— wherein y is an integer from 1 to 4 and the terminal CH$_2$ group of which is linked to the adjacent T in formula (10c); R$_{17}$ is H; R$_{18}$ is methyl, allyl, tolylmethyl or benzyl, R$_{19}$ is methyl, ethyl, benzyl or phenyl, or R$_{18}$ and R$_{19}$ together are pentamethylene, R$_{20}$ and R$_2$, are each independently of the other C$_1$–C$_4$-alkyl or R$_{20}$ and R$_{21}$ together are —CH$_2$CH$_2$OCH$_2$CH$_2$—, and R$_{16}$ is branched C$_6$–C$_{10}$-alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexylene-CH$_2$- or cyclohexylene-CH$_2$-substituted by from 1 to 3 methyl groups.

Some examples of especially preferred functional photoinitiators are the compounds of formulae

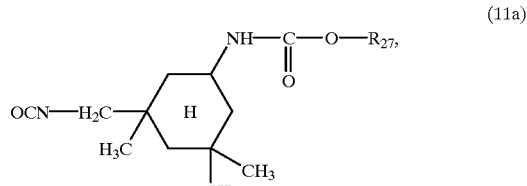
(11a)

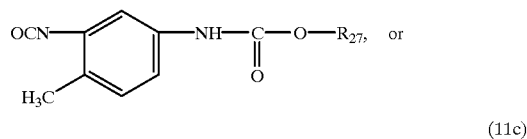
(11b)

(11c)

OCN—CH$_2$—C(CH$_3$)$_2$—CH$_2$—CH(CH$_3$)—CH$_2$—CH$_2$—NH—C(O)—O—R$_{27}$, wherein R$_{27}$ is a radical

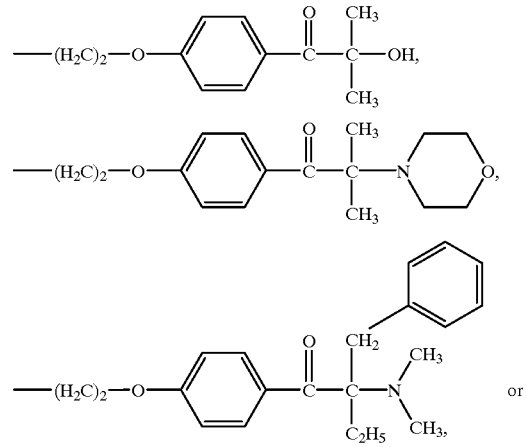

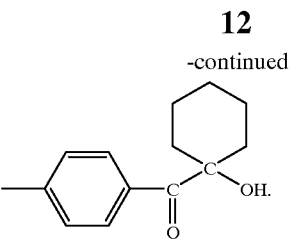

In a preferred embodiment of the invention, the covalent bonding between the bilayer(s) that is/are attached to the bulk material surface and the photoinitiator occurs via reaction of an amino or carboxy group, particularly an amino group, of the modified bulk material surface with an isocyanato group of the photoinitiator, for example using a photoinitiator of the above formula (10b), (10c), (11a), (11b) or (11c). Suitable methods for this are known, for example, from the above-mentioned documents. The reaction may be carried out, for example, at elevated temperature, for example from 0° to 100° C. and preferably at room temperature, and optionally in the presence of a catalyst. After the reaction, excess compounds can be removed, for example, with solvents.

According to a preferred embodiment of the invention the bulk material comprises on its modified surface —NH$_2$ and/or —NH— groups, that are coreactive with isocyanato groups, some of whose H atoms have been substituted by radicals of the formulae

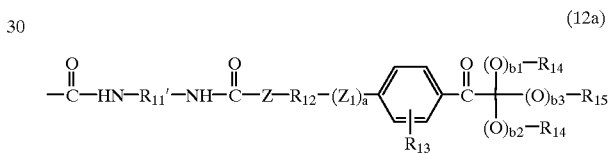
(12a)

or

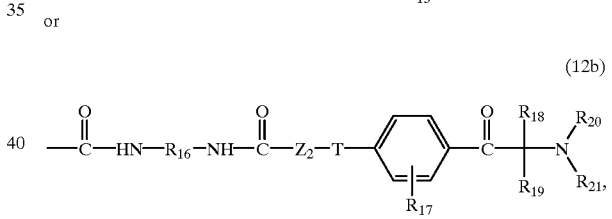
(12b)

wherein for the variables R$_{11}$'–R$_{21}$, T, Z, Z$_1$, Z$_2$, a, b1, b2 and b3 the above-given meanings and preferences apply.

In another embodiment of the invention, the covalent bonding between the modified bulk material surface and the photoinitiator occurs via reaction of a carboxy or isocyanato group of the bilayer attached to the bulk material with a hydroxy, amino or alkylamino group of the photoinitiator, for example using a photoinitiator of the above formula (10a). Isocyanato groups may be attached to the bilayer, for example, by first reacting an above-mentioned modified bulk material containing a bilayer with amino groups on the surface, selectively with one isocyanato group of a diisocyanate of formula OCN—R$_{11}$'—NCO, wherein R$_{11}$' has the above-given meanings; the thus modified bulk material then may be reacted with a photoinitiator of the above-mentioned formula (10a). The reaction of carboxy groups of the bilayer with hydroxy or amino groups of the photoinitiator of formula (10a) is well-known in the art and may be carried out, for example, as described in textbooks of organic chemistry.

A hydrophilic monomer useful to provide the hydrophilic surface coating (b) on the initiator-modified bulk material surface is typical a monomer that yields as homopolymer a polymer that is water-soluble or can absorb at least 10% by weight of water. Examples of preferred hydrophilic monomers are hydroxy-substituted $C_2$–$C_4$-alkyl acrylates and methacrylates, acrylamide, W methacrylamide, N,N-di-$C_1$–$C_4$-alkyl acrylamides and methacrylamides, ethoxylated acrylates and methacrylates, hydroxy-substituted $C_2$–$C_4$-alkyl acrylamides and methacrylamides, hydroxy-substituted $C_1$–$C_4$-alkyl vinyl ethers, sodium ethylenesulfonate, sodium styrenesulfonate, 2-acrylamido-2-methylpropanesulfonic acid, N-vinylpyrrole, N-vinylsuccinimide, N-vinylpyrrolidone, 2- or 4-vinylpyridine, acrylic acid, methacrylic acid, amino-(the term "amino" also including quaternary ammonium), mono-$C_1$–$C_4$-alkylamino- or di-$C_1$–$C_4$-alkylamino-$C_1$–$C_4$-alkyl acrylates and methacrylates, allylalcohol and the like. Hydroxy-substituted or N,N-di-$C_1$–$C_2$-alkylamino-substituted $C_2$–$C_4$alkyl(meth)acrylates, five- to seven-membered N-vinyl lactams, N,N-di-$C_1$–$C_4$alkyl(meth) acrylamides and vinylically unsaturated carboxylic acids having a total of from 3 to 5 carbon atoms, for example, are preferred.

Examples of preferred hydrophilic vinylic monomers include hydroxyethyl methacrylate, hydroxy-ethyl acrylate, acrylamide, methacrylamide, N,N-dimethylacrylamide, allyl alcohol, N-vinylpyrrolidone, acrylic acid, methacrylic acid and N,N-dimethylaminoethyl methacrylate.

Preferably the hydrophilic surface coating (b) on the bulk material (a) is obtained using a suitable macromonomer. A preferred macromonomer is, for example, of formula

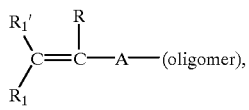
(1)

wherein $R_1$ is hydrogen, $C_1$–$C_6$-alkyl or a radical —COOR';

R, R' and $R_1'$ are each independently of the other hydrogen or $C_1$–$C_6$-alkyl;

A is a direct bond or is a radical of formula

(2a)

or

(2b);

or

(2c);

or

(2d);

or

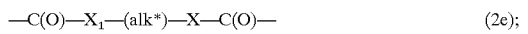
(2e);

or A and $R_1$, together with the adjacent double bond, are a radical of formula

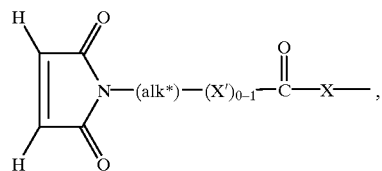
(2f)

$A_1$ is —O-$C_2$–$C_{12}$-alkylene which is unsubstituted or substituted by hydroxy, or is —O-$C_2$–$C_{12}$-alkylene-NH—C(O)— or —O-$C_2$–$C_{12}$-alkylene —O—C(O)—NH—$R_{11}$—NH—C(O)—, wherein $R_{11}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene;

and (oligomer) denotes (i) the radical of a telomer of formula

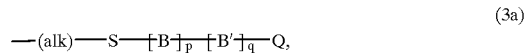
(3a)

wherein (alk) is $C_2$–$C_{12}$-alkylene,

Q is a monovalent group that is suitable to act as a polymerization chain-reaction terminator, p and q are each independently of another an integer from 0 to 250, wherein the total of (p+q) is an integer from 2 to 250, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

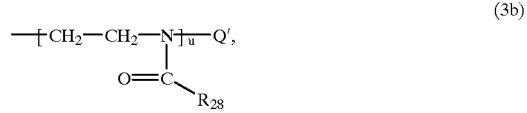
(3b)

wherein $R_{28}$ is hydrogen or unsubstituted or hydroxy-substituted $C_1$–$C_{12}$-alkyl, u is an integer from 2 to 250 and Q' is a radical of a polymerization initiator; or (iii) the radical of formula

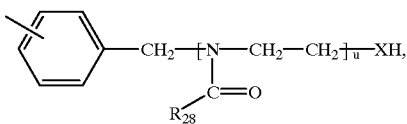

(3b')

wherein $R_{28}$, X and u are as defined above, or (iv) the radical of an oligomer of formula

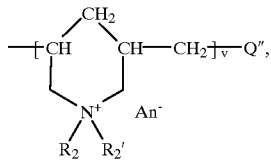

(3c)

wherein $R_2$ and $R_2'$ are each independently $C_1$–$C_4$-alkyl, $An^-$ is an anion, v is an integer from 2 to 250, and Q" is a monovalent group that is suitable to act as a polymerization chain-reaction terminator; or (v) the radical of an oligopeptide of formula

or

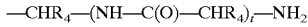

wherein $R_4$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH$_2$ and t is an integer from 2 to 250, or the radical of an oligopeptide based on proline or hydroxyproline; or (vi) the radical of a polyalkylene oxide of formula

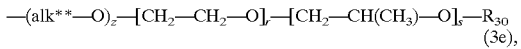

wherein $R_{30}$ is hydrogen or $C_1$–$C_{24}$-alkyl, (alk**) is $C_2$–$C_4$-alkylene, z is 0 or 1, r and s are each independently an integer from 0 to 250 and the total of (r+s) is from 2 to 250; or (vii) the radical of an oligosaccharide;
subject to the provisos that A is not a direct bond if (oligomer) is a radical of formula (3a);

A is a direct bond if (oligomer) is a radical of formula (3b');

A is not a radical of formula (2c) or (2e) if (oligomer) is a radical of formula (3b), (3c), (3d), (3e) or is the radical of an oligosaccharide; and A is a radical of formula (2c) or (2e) if (oligomer) is a radical of formula (3d').

The following preferences apply to the variables contained in the definition of the macromonomer of formula (1):

R' is preferably hydrogen or $C_1$–$C_4$-alkyl, more preferably hydrogen or $C_1$–$C_2$-alkyl and particularly preferably hydrogen.

$R_1$ is preferably hydrogen, methyl or carboxyl, and particularly preferably hydrogen.

R is preferably hydrogen or methyl.

X is preferably a bivalent group —O— or —NH—. X is particularly preferably the group —NH— if (oligomer) is a radical of formula (3a); (3c) or (3d), and is particularly preferably the group —O— if (oligomer) is a radical of formula (3b). X' is preferably —O— or —NH— and more preferably —NH—. $X_1$ is preferably —O— or —NH—.

$R_{11}$ as alkylene is preferably a linear or branched $C_3$–$C_{14}$alkylene radical, more preferably a linear or branched $C_4$–$C_{12}$alkylene radical and most preferably a linear or branched $C_1$–$C_{10}$alkylene radical.

When $R_{11}$ is arylene, it is, for example, naphthylene or especially phenylene, each of which may be substituted, for example, by $C_1$–$C_4$-alkyl or by $C_1$–$C_4$-alkoxy. Preferably, $R_{11}$ as arylene is 1,3- or 1,4-phenylene that is unsubstituted or substituted by $C_1$–$C_4$-alkyl or by $C_1$–$C_4$-alkoxy in the ortho-position to at least one linkage site. Examples of substituted arylene are 1-methyl-2,4-phenylene, 1,5-dimethyl-2,4-phenylene, 1-methoxy-2,4-phenylene and 1-methyl-2,7-naphthylene.

$R_{11}$ as aralkylene is preferably naphthylalkylene and most preferably phenylalkylene. The alkylene group in aralkylene contains preferably from 1 to 12, more preferably from 1 to 6 and most preferably from 1 to 4 carbon atoms. Most preferably, the alkylene group in aralkylene is methylene or ethylene.

When $R_{11}$ is cycloalkylene, it is preferably $C_5$–$C_6$cycloalkylene and most preferably cyclohexylene that is unsubstituted or substituted by methyl.

When $R_{11}$ is cycloalkylene-alkylene, it is preferably cyclopentylene-$C_1$–$C_4$-alkylene and especially cyclohexylene-$C_1$–$C_4$-alkylene, each unsubstituted or mono- or poly-substituted by $C_1$–$C_4$-alkyl, especially methyl. More preferably, the group cycloalkylene-alkylene is cyclohexylene-ethylene and, most preferably, cyclohexylene-methylene, each unsubstituted or substituted in the cyclohexylene radical by from 1 to 3 methyl groups.

When $R_{11}$ is alkylene-cycloalkylene-alkylene, it is preferably $C_1$–$C_4$-alkylene-cyclopentylene-$C_1$–$C_4$-alkylene and especially $C_1$–$C_4$-alkylene-cyclohexylene-$C_1$–$C_4$-alkylene, each unsubstituted or mono- or poly-substituted by $C_1$–$C_4$-alkyl, especially methyl. More preferably, the group alkylene-cycloalkylene-alkylene is ethylene-cyclohexylene-ethylene and, most preferably, is methylene-cyclohexylene-methylene, each unsubstituted or substituted in the cyclohexylene radical by from 1 to 3 methyl groups.

$R_{11}$ as $C_3$–$C_8$-cycloalkylene-$C_1$–$C_2$-alkylene-$C_3$–$C_8$-cycloalkylene or $C_6$–$C_{10}$-arylene-$C_1$–$C_2$-alkylene-$C_6$–$C_{10}$-arylene is preferably $C_5$–$C_6$-cycloalkylene-methylene-$C_5$–$C_6$-cycloalkylene or phenylene-methylene-phenylene, each of which may be unsubstituted or substituted in the cycloalkyl or phenyl ring by one or more methyl groups.

The radical $R_{11}$ has a symmetrical or, preferably, an asymmetrical structure. A preferred group of radicals $R_{11}$ comprises those, wherein $R_{11}$ is linear or branched $C_6$–$C_{10}$alkylene; cyclohexylene-methylene or cyclohexylene-methylene-cyclohexylene each unsubstituted or substituted in the cyclohexyl moiety by from 1 to 3 methyl groups; or phenylene or phenylene-methylene-phenylene each unsubstituted or substituted in the phenyl moiety by methyl. The bivalent radical $R_{11}$ is derived preferably from a diisocyanate and most preferably from a diisocyanate selected from the group isophorone diisocyanate (IPDI), toluylene-2,4-diisocyanate (TDI), 4,4'-methylenebis(cyclohexyl isocyanate), 1,6-diisocyanato-2,2,4-trimethyl-n-hexane (TMDI), methylenebis(phenyl isocyanate), methylenebis(cyclohexyl-4-isocyanate) and hexamethylene diisocyanate (HMDI).

Preferred meanings of $A_1$ are unsubstituted or hydroxy-substituted —O—$C_2$–$C_8$-alkylene or a radical —O—$C_2$–$C_6$-alkylene—NH—C(O)— and particularly —O—$(CH_2)_{2-4}$—, —O—$CH_2$—CH(OH)—$CH_2$— or a radical —O—$(CH_2)_{2-4}$—NH—C(O)—. A particularly preferred meaning of $A_1$ is the radical —O—$(CH_2)_2$—NH—C(O)—.

$A_2$ is preferably $C_1$–$C_6$-alkylene, phenylene or benzylene, more preferably $C_1$–$C_4$-alkylene and even more preferably $C_1$–$C_2$-alkylene.

n is an integer of 0 or preferably 1. m is preferably an integer of 1.

$R_1'$ is preferably hydrogen or methyl and particularly preferably hydrogen.

In case that (oligomer) is a radical of formula (3a), (3b), (3c), (3d), (3e) or is the radical of an oligosaccharide. A preferably denotes a radical of formula (2a) or (2b) and particularly preferably a radical of formula (2a), wherein the above given meanings and preferences apply for the variables contained therein.

A preferred group of hydrophilic macromonomers according to the invention comprises compounds of the above formula (1), wherein R is hydrogen or methyl, $R_1$ is hydrogen, methyl or carboxyl, $R_1'$ is hydrogen, A is a radical of the formula (2a) or (2b) and (oligomer) is a radical of formula (3a), (3b), (3c), (3d), (3e) or is the radical of an oligosaccharide. An even more preferred group of hydrophilic macromonomers comprises compounds of the above formula (1), wherein R is hydrogen or methyl, $R_1$ and $R_1'$ are each hydrogen, A is a radical of the formula (2a) and (oligomer) is a radical of formula (3a). A further group of preferred macromonomers comprises compounds of formula (1), wherein A is a radical of formula (2e) above and (oligomer) is a radical of formula (3a).

(alk) and (alk*) are each independently preferably $C_2$–$C_8$-alkylene, more preferably $C_2$–$C_6$-alkylene, even more preferably $C_2$–$C_4$-alkylene and particularly preferably 1,2-ethylene. The alkylene radicals (alk) and (alk*) may be branched or preferably linear alkylene radicals.

Q is for example hydrogen.

The total of (p+q) is preferably an integer from 2 to 150, more preferably from 5 to 100, even more preferably from 5 to 75 and particularly preferably from 10 to 50. In a preferred embodiment of the invention q is 0 and p is an integer from 2 to 250, preferably from 2 to 150, more preferably from 5 to 100, even more preferably from 5 to 75 and particularly preferably from 10 to 50. In a further preferred embodiment p is from 4 to 99, q is from 1 to 96 and the total 30 of (p+q) is from 5 to 100.

Suitable hydrophilic substituents of the radicals B or B' may be non-ionic, anionic, cationic or zwitterionic substituents. Accordingly, the telomer chain of formula (3a) that contains monomer units B and/or B' may be a charged chain containing anionic, cationic and/or zwitterionic groups or may be an uncharged chain. In addition, the telomer chain may comprise a copolymeric mixture of uncharged and charged units. The distribution of the charges within the telomer, if present, may be random or blockwise.

In one preferrred embodiment of the invention, the telomer radical of formula (3a) is composed solely of non-ionic monomer units B and/or B'. In another preferred embodiment of the invention, the telomer radical of formula (3a) is composed solely of ionic monomer units B and/or B', for example solely of cationic monomer units or solely of anionic monomer units. Still another preferred embodiment of the invention is directed to telomer radicals of formula (3a) comprising nonionic units B and ionic units B'.

Suitable non-ionic substituents of B or B' include for example a radical $C_1$–$C_6$-alkyl which is substituted by one or more same or different substituents selected from the group consisting of —OH, $C_1$–$C_4$-alkoxy and —$NR_9R_9'$, wherein $R_9$ and $R_1'$ are each independently of another hydrogen or unsubstituted or hydroxy-substituted $C_1$–$C_6$-alkyl or phenyl; phenyl which is substituted by hydroxy, $C_1$–$C_4$-alkoxy or —$NR_9R_9'$, wherein $R_1$ and $R_1'$ are as defined above; a radical —COOY, wherein Y is $C_1$–$C_{24}$-alkyl which is unsubstituted or substituted, for example, by hydroxy, $C_1$–$C_4$-alkoxy, —O—$Si(CH_3)_3$, —$NR_9R_9'$ wherein $R_1$ and $R_1'$ are as defined above, a radical —O—$(CH_2CH_{20})_{1-24}$-E wherein E is hydrogen or $C_1$–$C_6$-alkyl, or a radical —NH—C(O)—O—G, wherein —O—G is the radical of a saccharide with 1 to 8 sugar units or is a radical —O—$(CH_2CH_{20})_{1-24}$—E, wherein E is as defined above, or Y is $C_5$–$C_8$-cycloalkyl which is unsubstituted or substituted by $C_1$–$C_4$-alkyl or $C_1$–$C_4$-alkoxy, or is unsubstituted or $C_1$–$C_4$-alkyl- or $C_1$–$C_4$-alkoxy-substituted phenyl or $C_7$–$C_{12}$-aralkyl; —$CONY_1Y_2$ wherein $Y_1$ and $Y_2$ are each independently hydrogen, $C_1$–$C_{12}$-alkyl, which is unsubstituted or substituted for example by hydroxy, $C_1$–$C_4$-alkoxy or a radical —O—$(CH_2CH_{20})_{124}$-E wherein E is as defined above, or $Y_1$ and $Y_2$ together with the adjacent N-atom form a five- or six-membered heterocyclic ring having no additional heteroatom or one additional oxygen or nitrogen atom; a radical —$OY_3$, wherein $Y_3$ is hydrogen; or $C_1$–$C_{12}$-alkyl which is unsubstituted or substituted by —$NR_9R_9'$; or is a radical —C(O)—$C_1$–$C_4$-alkyl; and wherein $R_1$ and $R_9'$ are as defined above; or a five- to seven-membered heterocyclic radical having at least one N-atom and being bound in each case via said nitrogen atom.

Suitable anionic substituents of B or B' include for example $C_1$–$C_6$-alkyl which is substituted by —$SO_3H$, —$OSO_3H$, —$OPO_3H_2$ and —COOH; phenyl which is substituted by one or more same or different substituents selected from the group consisting of —$SO_3H$, —COOH, —OH and —$CH_2$—$SO_3H$; —COOH; a radical —$COOY_4$, wherein $Y_4$ is $C_1$–$C_{24}$-alkyl which is substituted for example by —COOH, —$SO_3H$, —$OSO_3H$, —$OPO_3H_2$ or by a radical —NH—C(O)—O—G' wherein G' is the radical of an anionic carbohydrate; a radical —$CONY_5Y_6$ wherein $Y_5$ is $C_1$–$C_{24}$-alkyl which is substituted by —COOH, —$SO_3H$, —$OSO_3H$, or —$OPO_3H_2$ and $Y_6$ independently has the meaning of $Y_5$ or is hydrogen or $C_1$–$C_{12}$-alkyl; or —$SO_3H$; or a salt thereof, for example a sodium, potassium, ammonium or the like salt thereof.

Suitable cationic substituents of B or B' include $C_1$–$C_{12}$-alkyl which is substituted by a radical —$NR_9R_9'R_9''^+An^-$, wherein $R_9R_9'$ and $R_9''$ are each independently of another hydrogen or unsubstituted or hydroxy-substituted $C_1$–$C_6$-alkyl or phenyl, and An is an anion; or a radical —$C(O)OY_7$, wherein $Y_7$ is $C_1$–$C_{24}$-alkyl which is substituted by —$NR_9R_9'R_9''^+An^-$ and is further unsubstituted or substituted for example by hydroxy, wherein $R_{11}R_9'$, $R_9''$ and $An^-$ are as defined above.

Suitable zwitterionic substituents of B or B' include a radical —$R_3$—Zw, wherein $R_3$ is a direct bond or a functional group, for example a carbonyl, carbonate, amide, ester, dicarboanhydride, dicarboimide, urea or urethane group; and Zw is an aliphatic moiety comprising one anionic and one cationic group each.

The following preferences apply to the hydrophilic substituents of B and B':

(i) non-ionic substituents:

Preferred alkyl substituents of B or B' are $C_1$–$C_4$-alkyl, in particular $C_1$–$C_2$-alkyl, which is substituted by one or more substituents selected from the group consisting of —OH and —NR$_9$R$_9$', wherein R$_9$ and R$_9$' are each independently of another hydrogen or C$_1$–C$_4$-alkyl, preferably hydrogen, methyl or ethyl and particularly preferably hydrogen or methyl, for example —CH$_2$—NH$_2$, —CH$_2$—N(CH$_3$)$_2$.

Preferred phenyl substituents of B or B' are phenyl which is substituted by —NH$_2$ or N(C$_1$–C$_2$-alkyl)$_2$, for example o-, m- or p-aminophenyl.

In case that the hydrophilic substituent of B or B' is a radical —COOY, Y as optionally substituted alkyl is preferably C$_1$–C$_{12}$-alkyl, more preferably C$_1$–C$_6$-alkyl, even more preferably C$_1$–C$_4$-alkyl and particularly preferably C$_1$–C$_2$-alkyl, each of which being unsubstituted or substituted as mentioned above. In case that the alkyl radical Y is substituted by —NR$_9$R$_9$', the above-given meanings and preferences apply for R$_9$ and R$_9$'. Examples of suitable saccharide substituents —O—G of the alkyl radical Y that is substituted by —NH—C(O)—O—G are the radical of a mono- or disaccharide, for example glucose, acetyl glucose, methyl glucose, glucosamine, N-acetyl glucosamine, glucono lactone, mannose, galactose, galactosamine, N-acetyl galactosamine, fructose, maltose, lactose, fucose, saccharose or trehalose, the radical of an anhydrosaccharide such as levoglucosan, the radical of a glucosid such as octylglucosid, the radical of a sugar alcohol such as sorbitol, the radical of a sugar acid derivative such as lactobionic acid amide, or the radical of an oligosaccharide with a maximum of 8 sugar units, for example fragments of a cyclodextrin, starch, chitosan, maltotriose or maltohexaose. The radical —O—G preferably denotes the radical of a mono- or disaccharide or the radical of a cyclodextrin fragment with a maximum of 8 sugar units. Particular preferred saccharide radicals —O—G are the radical of trehalose or the radical of a cyclodextrin fragment. In case that the alkyl radical Y is substituted by a radical —O—(CH$_2$CH$_2$O)$_{1–24}$—E or —NH—C(O)—O—G wherein —O—G is —O—(CH$_2$CH$_2$O)$_{24}$-E, the number of (CH$_2$CH$_2$O) units is preferably from 1 to 12 in each case and more preferably from 2 to 8. E is preferably hydrogen or C$_1$–C$_2$-alkyl.

Y as C$_5$–C$_8$-cycloalkyl is for example cyclopentyl or preferably cyclohexyl, each of which being unsubstituted or substituted for example by 1 to 3 C$_1$–C$_2$-alkyl groups. Y as C$_7$–C$_{12}$-aralkyl is for example benzyl.

Preferred nonionic radicals —COOY are those wherein Y is C$_1$–C$_4$-alkyl; or C$_2$–C$_4$-alkyl which is substituted by one or two substituents selected from the group consisting of hydroxy; C$_1$–C$_2$-alkoxy; —O—Si(CH$_3$)$_3$; and —NR$_9$R$_9$' wherein R$_9$ and R$_1$' are each independently of another hydrogen or C$_1$–C$_4$-alkyl; or Y is a radical —CH$_2$CH$_2$—O—(CH$_2$CH$_2$O)$_{1,12}$-E wherein E is hydrogen or C$_1$–C$_2$-alkyl; or is a radical -C$_2$–C$_4$-alkylene—NH—C(O)—O—G, wherein —O—G is the radical of a saccharide.

More preferred non-ionic radicals —COOY are those wherein Y is C$_1$–C$_2$-alkyl, particularly methyl; or C$_2$–C$_4$-alkyl which is substituted by one or two substituents selected from the group consisting of —OH and —NR$_9$R$_9$' wherein R$_9$ and R$_9$' are each independently of another hydrogen or C$_1$–C$_2$-alkyl; or a radical —CH$_2$CH$_2$—O—(CH$_2$CH$_2$O)$_{112}$—E wherein E is hydrogen or C$_1$–C$_2$-alkyl; or is a radical —C$_2$–C$_4$-alkylene—NH—C(O)—O—G wherein —O—G is the radical of a saccharide.

Particularly preferred radicals —COOY comprise those wherein Y is C$_2$–C$_3$-alkyl, which is substituted by hydroxy or N,N-di-C$_1$–C$_2$-alkylamino, or is a radical -C$_2$–C$_3$-alkylene—NH—C(O)—O—G wherein —O—G is the radical of trehalose.

Preferred non-ionic substituents —C(O)—NY$_1$Y$_2$ of B or B' are those wherein Y$_1$ and Y$_2$ are each independently of the other hydrogen or C$_1$–C$_4$-alkyl which is unsubstituted or substituted by hydroxy; or Y$_1$ and Y$_2$ together with the adjacent N-atom form a heterocyclic 6-membered ring having no further heteroatom or having one further N- or O-atom. Even more preferred meanings of Y$_1$ and Y$_2$, independently of each other, are hydrogen or C$_1$–C$_2$-alkyl which is unsubstituted or substituted by hydroxy; or Y$_1$ and Y$_2$ together with the adjacent N-atom form a N-C$_1$–C$_2$-alkyl-piperazino or morpholino ring. Particularly preferred non-ionic radicals —C(O)—NY$_1$Y$_2$ are those wherein Y$_1$ and Y$_2$ are each independently of the other hydrogen or C$_1$–C$_2$-alkyl; or Y$_1$ and Y$_2$ together with the adjacent N-atom form a morpholino ring.

Preferred non-ionic substituents —OY$_3$ of B or B' are those wherein Y$_3$ is hydrogen, C$_1$–C$_4$-alkyl which is unsubstituted or substituted by —NH$_2$ or —N(C$_1$–C$_2$-alkyl)$_2$, or is a group —C(O)C$_1$–C$_2$-alkyl. Y$_3$ is particularly preferred hydrogen or acetyl.

Preferred non-ionic heterocyclic substituents of B or B' are a 5- or 6-membered heteroaromatic or heteroaliphatic radical having one N-atom and in addition no further heteroatom or an additional N- or O-heteroatom, or is a 5 to 7-membered lactame. Examples of such heterocyclic radicals are N-pyrrolidonyl, 2- or 4-pyridinyl, 2-methyl pyridin-5-yl, 2-, 3-oder 4-hydroxypyridinyl, N-ε-caprolactamyl, N-imidazolyl, 2-methylimidazol-1-yl, N-morpholinyl or 4—N-methylpiperazin-1-yl, particularly N-morpholinyl or N-pyrrolidonyl.

A group of preferred non-ionic substituents of B or B' comprises C$_1$–C$_2$-alkyl, which is unsubstituted or substituted by —OH or —NR$_9$R$_9$', wherein R$_9$ and R$_9$' are each independently of the other hydrogen or C$_1$–C$_2$-alkyl; a radical —COOY wherein Y is C$_1$–C$_4$-alkyl; C$_2$–C$_4$-alkyl which is substituted by —OH or —NR$_9$R$_9$' wherein R$_9$ and R$_9$' are each independently of another hydrogen or C$_1$–C$_2$-alkyl, or Y is a radical -C$_2$–C$_4$-alkylene—NH—C(O)—O—G wherein —O—G is the radical of a saccharide; a radical —C(O)—NY$_1$Y$_2$, wherein Y$_1$ and Y$_2$ are each independently of the other hydrogen or C$_1$–C$_4$-alkyl which is unsubstituted or substituted by hydroxy, or Y$_1$ and Y$_2$ together with the adjacent N-atom form a heterocyclic 6-membered ring having no further heteroatom or having one further N- or O-atom; a radical —OY$_3$, wherein Y$_3$ is hydrogen, C$_1$–C$_4$-alkyl which is unsubstituted or substituted by —NH$_2$ or —N(C$_1$–C$_2$-alkyl)$_2$, or is a group —C(O) C$_1$–C$_2$-alkyl; or a 5- or 6-membered heteroaromatic or heteroaliphatic radical having one N-atom and in addition no further heteroatom or an additional N-, O- or S-heteroatom, or a 5 to 7-membered lactame.

A group of more preferred non-ionic substituents of B or B' comprises a radical —COOY, wherein Y is C$_1$–C$_2$-alkyl, C$_2$–C$_3$-alkyl, which is substituted by hydroxy, amino or N,N-di-C$_1$–C$_2$-alkylamino, or is a radical -C$_2$–C$_4$-alkylene—NH—C(O)—O—G wherein —O—G is the radical of trehalose; a radical —CO-NY$_1$Y$_2$, wherein Y$_1$ and Y$_2$ are each independently of the other hydrogen or C$_1$–C$_2$-alkyl which is unsubstituted or substituted by hydroxy, or Y$_1$ and Y$_2$ together with the adjacent N-atom form a N-C$_1$–C$_2$-alkylpiperazino or morpholino ring; or a heterocyclic radical selected from the group consisting of N-pyrrolidonyl, 2- or 4-pyridinyl, 2-methylpyridin-5-yl, 2-, 3-oder 4-hydroxypyridinyl, N-s-caprolactamyl, N-imidazolyl, 2-methylimidazol-1-yl, N-morpholinyl and 4—N-methylpiperazin-1-yl.

A particularly preferred group of non-ionic substituents of B or B' comprises the radicals —CONH$_2$, —CON(CH$_3$)$_2$, —CONH—(CH$_2$)$_2$—OH,

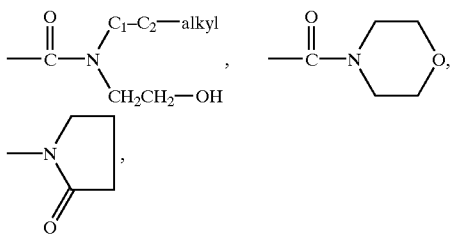

—COO—(CH$_2$)$_2$—N(CH$_3$)$_2$, and —COO(CH$_2$)$_{2-4}$—NHC(O)—O—G wherein —O—G is the radical of trehalose.

(ii) Anionic Substituents:

Preferred anionic substituents of B or B' are C$_1$–C$_4$-alkyl, in particular C$_1$–C$_2$-alkyl, which is substituted by one or more substituents selected from the group consisting of —SO$_3$H and —OPO$_3$H$_2$, for example —CH$_2$—SO$_3$H; phenyl which is substituted by —SO$_3$H or sulfomethyl, for example o-, m- or p-sulfophenyl or o-, m- or p-sulfomethylphenyl; —COOH; a radical —COOY$_4$, wherein Y$_4$ is C$_2$–C$_6$-alkyl which is substituted by —COOH, —SO$_3$H, —OSO$_3$H, —OPO$_3$H$_2$, or by a radical —NH—C(O)—O—G' wherein G' is the radical of lactobionic acid, hyaluronic acid or sialic acid, in particular C$_2$–C$_4$-alkyl which is substituted by —SO$_3$H or —OSO$_3$H; a radical —CONY$_5$Y$_6$ wherein Y$_5$ is C$_1$–C$_6$-alkyl substituted by sulfo, in particular C$_2$–C$_4$-alkyl substituted by sulfo, and Y$_6$ is hydrogen, for example the radical —C(O)—NH—C(CH$_3$)$_2$—CH$_2$—SO$_3$H; or —SO$_3$H; or a suitable salt thereof. Particular preferred anionic substituents of B or B' are —COOH, —SO$_3$H, o-, m- or p-sulfophenyl, o-, m- or p-sulfomethylphenyl or a radical —CONY$_5$Y$_6$ wherein Y$_5$ is C$_2$–C$_4$-alkyl substituted by sulfo, and Y$_6$ is hydrogen, especially carboxy.

(iii) Cationic Substituents:

Preferred cationic substituents of B or B' are C$_1$–C$_4$-alkyl, in particular C$_1$–C$_2$-alkyl, which is in each case substituted by —NR$_9$R$_9$'R$_9$''$^+$An$^-$; or a radical —C(O)OY$_7$ wherein Y$_7$ is C$_2$–C$_6$-alkyl, in particular C$_2$–C$_4$-alkyl, which is in each case substituted by —NR$_9$R$_9$'R$_9$''$^+$An$^-$ and is further unsubstituted or substituted by hydroxy. R$_9$, R$_9$' and R$_9$'' are each independently of another preferably hydrogen or C$_1$–C$_4$-alkyl, more preferably methyl or ethyl and particularly preferably methyl. Examples of suitable anions An$^-$ are Hal$^-$, wherein Hal is halogen, for example Br$^-$, F$^-$, J$^-$ or particularly Cl$^-$, furthermore HCO$_3^-$, CO$_3^{2-}$, H$_2$PO$_3^-$, HPO$_3^{2-}$, PO$_3^{3-}$, HSO$_4^-$, SO$_4^{2-}$ or the radical of an organic acid such as OCOCH$_3^-$ and the like. A particularly preferred cationic substituent of B or B' is a radical —C(O)OY$_7$ wherein Y$_7$ is C$_2$–C$_4$-alkyl, which is substituted by —N(C$_1$–C$_2$-alkyl)$_3^+$An$^-$ and is further substituted by hydroxy, and An$^-$ is an anion, for example the radical —C(O)O—CH$_2$— CH(OH)—CH$_2$—N(CH$_3$)$_3^+$An$^-$.

(iv) Zwitterionic Substituents -R$_3$-Zw:

R$_3$ is a preferably a carbonyl, ester or amide functional group and more preferably an ester group —C(O)—O—.

Suitable anionic groups of the moiety Zw are for example —COO$^-$, —SO$_3$—, —OSO$_3$—, —OPO$_3$H$^-$ or bivalent —O—PO$_2^-$— or —O—PO$_2^-$—O—, preferably a group —COO— or —SO$_3$— or a bivalent group —O—PO$_2^-$—, and in particular a group —SO$_3$—.

Suitable cationic groups of the moiety Zw are for example a group —NR$_9$R$_9$'R$_9$''$^+$or a bivalent group —NR$_9$R$_9$'$^+$—, wherein R$_{11}$R$_1$' and R$_9$'' are as defined above, and are each independently of the other, preferably hydrogen or C$_1$–C$_6$-alkyl, preferably hydrogen or C$_1$–C$_4$-alkyl and most preferably each methyl or ethyl.

The moiety Zw is for example C$_2$–C$_{30}$-alkyl, preferably C$_2$–C$_{12}$-alkyl, and more preferably C$_3$–C$_8$-alkyl, which is in each case uninterrupted or interrupted by —O— and substituted or interrupted by one of the above-mentioned anionic and cationic groups each, and, in addition, is further unsubstituted or substituted by a radical —OY$_8$, wherein Y$_8$ is hydrogen or the acyl radical of a carboxylic acid.

Y$_8$ is preferably hydrogen or the acyl radical of a higher fatty acid.

Zw is preferably C$_2$–C$_{12}$-alkyl and even more preferably C$_3$–C$_8$-alkyl which is substituted or interrupted by one of the above-mentioned anionic and cationic groups each, and in addition may be further substituted by a radical —OY$_8$.

A preferred group of zwitter-ionic substituents -R$_3$-Z corresponds to the formula

or

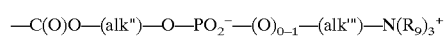

wherein R$_9$ is hydrogen or C$_1$–C$_6$-alkyl; An$^-$ is an anionic group —COO—, —SO$_3^-$, —OSO$_3^-$ or —OPO$_3$H$^-$, preferably —COO$^-$ or —SO$_3^-$ and most preferably —SO$_3^-$, alk' is C$_1$–C$_{12}$-alkylene, (alk'') is C$_2$–C$_{24}$-alkylene which is unsubstituted or substituted by a radical —OY$_8$, Y$_8$ is hydrogen or the acyl radical of a carboxylic acid, and (alk''') is C$_2$–C$_8$-alkylene.

(alk') is preferably C$_2$–C$_8$-alkylene, more preferably C$_2$–C$_6$-alkylene and most preferably C$_2$–C$_4$-alkylene. (alk'') is preferably C$_2$–C$_{12}$-alkylene, more preferably C$_2$–C$_6$-alkylene and particularly preferably C$_2$–C$_3$-alkylene which is in each case unsubstituted or substituted by hydroxy or by a radical —OY$_8$. (alk''') is preferably C$_2$–C$_4$-alkylene and more preferably C$_2$–C$_3$-alkylene. R$_9$ is hydrogen or C$_1$–C$_4$-alkyl, more preferably methyl or ethyl and particularly preferably methyl. A preferred zwitterionic substituent of B or B' is of formula

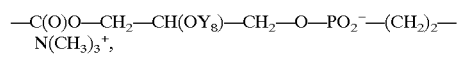

wherein Y$_8$ is hydrogen or the acyl radical of a higher fatty acid.

In one embodiment of the invention one of B and B' may also be the radical of a hydrophobic comonomer which includes especially those customarily used in the manufacture of contact lenses. Suitable hydrophobic vinylic comonomers include, without the list being exhaustive acrylonitrile, methacrylonitrile, vinyl-C$_1$–C$_{18}$-alkanoates, C$_2$–C$_{18}$-alkenes, C$_2$–C$_{18}$-haloalkenes, styrene, C$_1$–C$_6$-alkylstyrene, C$_2$–C$_{10}$-perfluoroalkyl acrylates and methacrylates or correspondingly partially fluorinated acrylates and methacrylates, C$_3$–C$_{12}$-perfluoroalkyl-ethyl-thiocarbonylaminoethyl acrylates and methacrylates, acryloxy- and methacryloxy-alkylsiloxanes, N-vinylcarbazole and the like. Examples of suitable hydrophobic vinylic comonomers include acrylonitrile, methacrylonitrile, vinyl acetate, vinyl propionate, vinylbutyrate, vinyl valerate, styrene, chloroprene, vinyl chloride, vinylidene chloride, 1-butene, butadiene, vinyltoluene, perfluorohexylethylthiocarbonylaminoethyl methacrylate, trifluoroethyl methacrylate, hexafluoroisopropyl methacrylate, hexafluorobutyl methacrylate, tris-trimethylsilyloxy-silyl-propyl methacrylate, 3-methacryloxypropylpentamethyidisiloxane and bis(methacryloxypropyl)-tetramethyldisiloxane.

B denotes for example a radical of formula

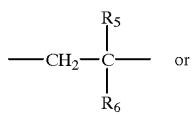
(4a)

or

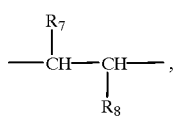
(4b)

wherein $R_5$ is hydrogen or $C_1$–$C_4$-alkyl, preferably hydrogen or methyl; $R_6$ is a hydrophilic substituent, wherein the above given meanings and preferences apply; $R_7$ is $C_1$–$C_4$-alkyl, phenyl or a radical —C(O)O$Y_9$, wherein $Y_9$ is hydrogen or unsubstituted or hydroxy-substituted $C_1$–$C_4$-alkyl; and $R_8$ is a radical —C(O)Y,' or —CH$_2$—C(O)O$Y_9$' wherein $Y_9$' independently has the meaning of $Y_9$.

$R_7$ is preferably $C_1$–$C_2$-alkyl, phenyl or a group —C(O)O$Y_9$. $R_8$ is preferably a group —C(O)O$Y_9$' or —CH$_2$—C(O)O$Y_9$' wherein $Y_9$ and $Y_9$' are each independently of the other hydrogen, $C_1$–$C_2$-alkyl or hydroxy-$C_1$–$C_2$-alkyl. Particularly preferred —CHR$_7$—CHR$_8$— units according to the invention are those wherein $R_7$ is methyl or a group —C(O)O$Y_9$ and $R_8$ is a group —C(O)O$Y_9$' or —CH$_2$—C(O)O$Y_9$ wherein $Y_9$ and $Y_9$' are each hydrogen, $C_1$–$C_2$-alkyl or hydroxy-$C_1$–$C_2$-alkyl.

B' independently may have one of the meanings given above for B or is the radical of a hydrophobic comonomer, for example the radical of one of the above-given hydrophobic comonomers.

If (oligomer) is a telomer radical of formula (3a), the radical -(alk)—S—[B]$_p$-[B']$_q$-Q preferably denotes a radical of formula

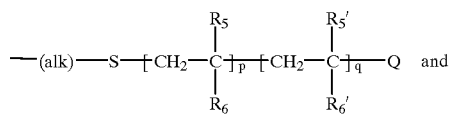
(3a')

and even more preferably of the formula

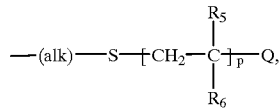
(3a'')

wherein for $R_5$, $R_6$, Q, p and q the above-given meanings and preferences apply, for $R_5$' independently the meanings and preferences given before for $R_5$ apply, and for $R_6$' independently the meanings and preferences given before for $R_6$ apply or $R_6$' is a hydrophobic substituent selected from the group consisting of hydrogen, —CN, $C_1$–$C_{18}$-alkanoyl, $C_1$–$C_{16}$-alkyl, $C_1$–$C_{16}$-haloalkyl, phenyl, $C_1$–$C_6$-alkylphenyl, $C_2$–$C_{10}$-perfluoroalkyloxycarbonyl or a corresponding partially fluorinated alkyloxycarbonyl radical, $C_3$–$C_{12}$-perfluoroalkyl-ethyl-thiocarbonylaminoethyloxycarbonyl, alkylsiloxyloxycarbonyl and carbazolyl A preferred group of suitable hydrophilic macromers according to the invention comprises compounds of the above formula (1) wherein R is hydrogen or methyl, $R_1$ is hydrogen, methyl or carboxyl, $R_1$' is hydrogen, A is a radical of the above formula (2a), (2b) or (2e), wherein n and m are each 0 or 1, X and X, are each independently of the other —O— or —NH—, $A_1$ is unsubstituted or hydroxy-substituted —O-$C_2$–$C_8$-alkylene or a radical —O-$C_2$–$C_6$-alkylene—NH—C(O)—, $A_2$ is $C_1$–$C_4$-alkylene, phenylene or benzylene, (alk*) is $C_2$–$C_4$-alkylene, and (oligomer) denotes a radical of formula

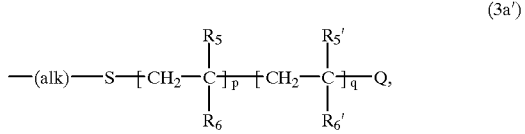
(3a')

wherein (alk) is $C_2$–$C_6$-alkylene, Q is a monovalent group that is suitable to act as a polymerization chain-reaction terminator, p and q are each an integer of from 0 to 100 and the total of (p+q) is from 5 to 100, $R_5$ and $R_5$' are each independently of the other hydrogen or methyl, and for $R_6$ and $R_6$' each independently of the other the meanings and preferences given before apply. One particularly preferred embodiment of the above outlined hydrophilic macromers comprises those wherein q is 0, p is from 5 to 100, $R_5$ is hydrogen or methyl, and $R_6$ is a radical —CONH$_2$, —CON(CH$_3$)$_2$, —CONH—(CH$_2$)$_2$—OH,

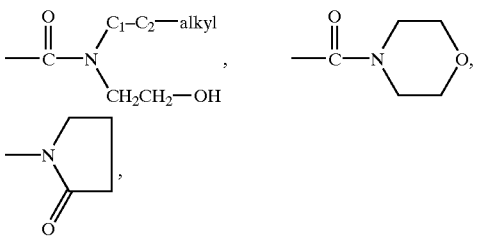

—COO—(CH$_2$)$_2$—N(CH$_3$)$_2$, or —COO(CH$_2$)$_{2-4}$—NHC(O)—O—G wherein —O—G is the radical of trehalose. A further preferred embodiment of the above outlined hydrophilic macromers comprises those wherein p is from 4 to 99, q is from 1 to 96 wherein in the total of (p+q) is from 5 to 100, $R_5$ and $R_5$' are each independently hydrogen or methyl, $R_6$ is a radical —CONH$_2$, —CON(CH$_3$)$_2$, —CONH—(CH$_2$)$_2$—OH,

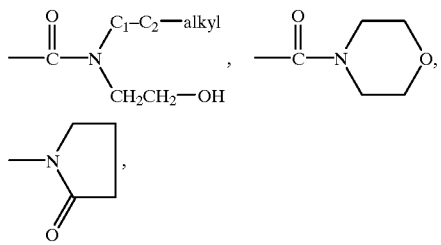

—COO—(CH$_2$)$_2$—N(CH$_3$)$_2$, or —COO(CH$_2$)$_{2-4}$—NHC(O)—O—G wherein —O—G is the radical of trehalose, and $R_6$' independently has the meaning of $R_1$ or is carboxy, subject to the proviso that $R_6$ and $R_6$' are different.

A more preferred group of suitable hydrophilic macromonomers according to the invention comprises compounds of formula

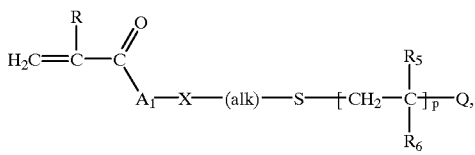

(1a)

wherein R is hydrogen or methyl, $A_1$ is —O—$(CH_2)_{2-4}$—, —O—$CH_2$—CH(OH)—$CH_2$— or a radical —O—$(CH_2)_{2-4}$—NH—C(O)—, X is —O— or —NH—, (alk) is $C_2$–$C_4$-alkylene, Q is a monovalent group that is suitable to act as a polymerization chain-reaction terminator, p is an integer from 5 to 50, $R_5$ is hydrogen or methyl, and for $R_6$ the above given meanings and preferences apply.

A particularly preferred embodiment of the invention relates to hydrophilic macromonomers of the formula

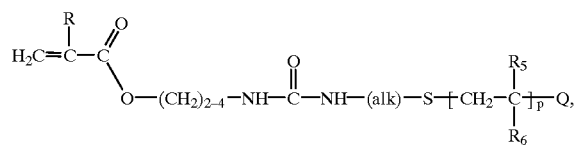

(1b)

wherein for R, $R_5$, $R_6$, Q, (alk) and p the above-given meanings and preferences apply. A particularly preferred group of hydrophilic macromonomers are compounds of the above formula (1b) wherein R is hydrogen or methyl, (alk) is $C_2$–$C_4$-alkylene, $R_5$ is hydrogen or methyl, p is an integer of 5 to 50, Q is as defined before, and for $R_6$ the above given meanings and preferences apply.

If (oligomer) is a radical (ii) of formula (3b), Q' in formula (3b) is for example $C_1$–$C_{12}$-alkyl, phenyl or benzyl, preferably $C_1$–$C_2$-alkyl or benzyl and in particular methyl. $R_{29}$ is preferably unsubstituted or hydroxy-substituted $C_1$–$C_4$-alkyl and in particular methyl. u is preferably an integer from 2 to 150, more preferably from 5 to 100, even more preferably from 5 to 75 and particularly preferably from 10 to 50.

If (oligomer) is a radical of formula (3b'), the above given meanings and preferences apply for the variables X, $R_{29}$ and u contained therein.

If (oligomer) denotes a radical (iv) of formula (3c), $R_2$ and $R_2'$ are each preferably ethyl or in particular methyl; v is preferably an integer from 2 to 150, more preferably from 5 to 100, even more preferably from 5 to 75 and particularly preferably from 10 to 50; Q'' is for example hydrogen; and $An^-$ is as defined before.

If (oligomer) denotes an oligopeptide radical (v) of formula (3d) or 3d'), $R_4$ is for example hydrogen, methyl, hydroxymethyl, carboxymethyl, 1-hydroxyethyl, 2-carboxyethyl, isopropyl, n-, sec. or iso-butyl, 4-amino-n-butyl, benzyl, p-hydroxybenzyl, imidazolylmethyl, indolylmethyl or a radical —$(CH_2)_3$—NH—C(=NH)—$NH_2$. t is preferably an integer from 2 to 150, more preferably from 5 to 100, even more preferably from 5 to 75 and particularly preferably from 10 to 50.

If (oligomer) denotes a polyoxyalkylene radical (vi) of formula (3e), $R_{30}$ is preferably hydrogen or $C_1$–$C_{18}$-alkyl, more preferably hydrogen or $C_1$–$C_{12}$-alkyl, even more preferably hydrogen, methyl or ethyl, and particularly preferably hydrogen or methyl. (alk**) is preferably a $C_2$–$C_3$-alkylene radical. z is preferably 0. r and s are each independently preferably an integer from 0 to 100 wherein the total of (r+s) is 5 to 100. r and s are each independently more preferably an integer from 0 to 50 wherein the total of (r+s) is 8 to 50. In a particularly preferred embodiment of the polyoxyalkylene radicals (oligomer), r is an integer from 8 to 50 and particularly 9 to 25, and s is 0.

(oligomer) as the radical of an oligosaccharide (vii) may be, for example, a di- or polysaccharide including carbohydrate containing fragments from a biopolymer. Examples are the radical of a cyclodextrin, trehalose, cellobiose, maltotriose, maltohexaose, chitohexaose or a starch, hyaluronic acid, deacetylated hyaluronic acid, chitosan, agarose, chitin 50, amylose, glucan, heparin, xylan, pectin, galactan, glycosaminoglycan, mucin, dextran, aminated dextran, cellulose, hydroxyalkylcellulose or carboxyalkylcellulose oligomer, each of which with a molecular weight average weight of, for example, up to 25000, preferably up to 10000. Preferably the oligosaccharide according to (vii) is the radical of a cyclodextrin with a maximum of 8 sugar units.

In the above formulae (2a), (2b), (2c), (2d) and (2e), the left bond is in each case attached to the double bond whereas the right bond is linked to the oligomer. Formulae (3a), (3a') and (3e) are to be understood as a statistic description of the respective oligomeric radicals, that is to say, the orientation of the monomers and the sequence of the monomers (in case of copolymers) are not fixed in any way by said formulae. The arrangement of B and B' in formula (3a) or of the ethyleneoxide and propyleneoxide units in formula (3e) thus may be random or blockwise. Throughout the whole description, anions such as —COOH or —$SO_3H$ groups always include suitable salt forms, preferably biomedical or especially ophthalmically acceptable salts, in particular —$COO^-Ka^+$ and —$SO_3^-Ka^+$ groups wherein $Ka^+$ is a cation such as an alkali metal cation or an ammonium cation.

The weight average molecular weight of the macromonomers of the invention depends principally on the desired properties and is for example from 300 to 50000, preferably from 300 to 12000, more preferably from 300 to 8000, even more preferably 300 to 5000, and particularly preferably from 500 to 2000.

The macromonomers of formula (1) may be prepared by methods, for example as described in WO 99/57581.

The hydrophilic monomers and macromonomers may be applied to the initiator-modified bulk material surface and polymerized there according to processes known per se. For example, the bulk material is immersed in a solution of the monomer or macromonomer, or a layer of monomer or macromonomer is first of all deposited on the modified bulk material surface, for example, by dipping, spraying, spreading, knife coating, pouring, rolling, spin coating or vacuum vapor deposition. The polymerization of the macromonomer on the bulk material surface then may be initiated, for example, thermally by the action of heat or preferably by irradiation, particularly by UV radiation. Suitable light sources for the irradiation are known to the artisan and comprise for example mercury lamps, high pressure mercury lamps, xenon lamps, carbon arc lamps or sunlight. The time period of irradiation may depend for example on the desired properties of the resulting composite material but is usually in the range of up to 30 minutes, preferably from 10 secondes to 10 minutes, and particularly preferably from 0.5 to 5 minutes. The irradiation may be carried out under ambient conditions or in an atmosphere of an inert gas, for example nitrogen. After the polymerization, any non-covalently bonded polymers, oligomers or non-reacted monomer or macromonomers formed can be removed, for example by treatment with suitable solvents.

By means of the above-described coating process, hydrophilic monomers may be grafted to the bulk material surface with formation of a coating having for example a so-called brush-type structure.

Most important, the grafting of the macromonomers to the bulk material surface yields a coating having for example a so-called bottle brush-type structure (BBT) composed of tethered "hairy" chains. Such BBT structures in one embodiment comprise a long hydrophilic or hydrophobic backbone which carries relatively densely packed comparatively short hydrophilic side chains (called primary bottle brushes). Another embodiment relates to secondary bottle brushes which are characterized in that the hydrophilic side chains themselves carry densely packed hydrophilic "secondary" side chains. Polymeric coatings of said primary and secondary BBT structures to a certain extent mimic highly water-retaining structures occurring in the human body, for example in cartilage or mucosal tissue.

The coating thickness of the hydrophilic surface coating (b) depends principally on the desired properties. In case of macromonomers it can be used, for example, from 0.001 to 1000 $\mu$m, preferably from 0.01 to 500 $\mu$m, more preferably from 0.01 to 100 $\mu$m, even more preferably from 0.05 to 50 $\mu$m, especially preferably from 0.1 to 5 $\mu$m and particularly preferably from 0.1 to 1 $\mu$m. A particularly suitable range is from 0.2 to 0.6 $\mu$m.

The complete coating of the bulk material according to the invention consists (a) of a polyionic material comprising one polyelectrolyte or preferably one or more bilayers of polyelectrolytes and (b) of an upper hydrophilic coating obtainable by grafting one or more hydrophilic monomers or 20 preferably macromonomers onto the surface, wherein the latter makes up at least 50%, preferably from 75 to 98% and particularly preferably from 80 to 95% of the total thickness of the fully hydrated coating.

A further embodiment of the invention is a biomedical device, e.g. an ophthalmic device, preferably a contact lens including both hard and particularly soft contact lenses, an intraocular lens or artificial cornea, comprising a composite material according to the invention and particular a composite material comprising a macromonomer-based surface coating. The inventive materials are further useful for example as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

The biomedical devices, e.g. ophthalmic devices according to the invention have a variety of unexpected advantages over those of the prior art which make those devices very suitable for practical purposes, e.g. as contact lens for extended wear or intraocular lens. For example, they do have a high surface wettability which can be demonstrated by their contact angles, their water retention ability and their water-film break up time or tear film break up time (TBUT).

The TBUT plays an particularly important role in the field of ophthalmic devices such as contact lenses. Thus the facile movement of an eyelid over a contact lens has proven important for the comfort of the wearer; this sliding motion is facilitated by the presence of a continuous layer of tear fluid on the contact lens, a layer which lubricates the tissue/lens interface. However, clinical tests have shown that currently available contact lenses partially dry out between blinks, thus increasing friction between eyelid and the lens. The increased friction results in soreness of the eyes and reduced movement of the contact lenses. Taking into account the average time period between two blinks of an eye it follows that a wettable and biocompatible contact lens should hold a continuous layer of tear fluid for more than 10 seconds and preferably for more than 15 seconds. Whereas current biomedical materials in general have TBUTs of well below 10 seconds and thus do not reach this target, the composite materials of the present invention have TBUTs of >10 seconds and especially >15 seconds. In addition, the TBUT of commercial contact lenses may be improved considerably by applying a surface coating according to the invention. For example, the TBUT of commercial contact lenses such as Focus Dailies™, Focus New Vues® or Lotrafilcon A lenses, may be increased by more than 50% or, according to a particularly preferred embodiment, by $\geq$100% by applying a surface coating according to the invention. On the base curve of a contact lens, the pronounced lubricity of the coating facilitates the on-eye lens movement which is essential for extended wear of contact lenses. Moreover, the composite materials of the invention provide additional effects being essential for lenses for extended wear, such as an increased thickness of the pre-lens tear film and of the topical lipid layer of the tear film which each contributes substantially to low microbial adhesion and resistance to deposit formation. Due to the extremely soft and lubricious character of the novel surface coatings, biomedical articles such as in particular contact lenses made from an inventive composite material show a superior wearing comfort including improvements with respect to late day dryness, long term (overnight) wear and acute vision on awake. The novel surface coatings moreover interact in a reversible manner with occular mucus which contributes to the improved wearing comfort.

In addition, biomedical devices, e.g. ophthalmic devices such as contact lenses, comprising a composite material of the invention have a very pronounced biocompatibility combined with good mechanical properties. For example, the devices are blood compatible and have a good tissue integration. In addition, there are generally no adverse eye effects observed, while the adsorption of proteins or lipids is low, also the salt deposit formation is lower than with conventional contact lenses. Generally, there is low fouling, low microbial adhesion and low bioerosion while good mechanical properties can be for example found in a low friction coefficient and low abrasion properties. Moreover, the dimensional stability of the composite materials of the invention is excellent. In addition, the attachment of a hydrophilic surface coating at a given bulk material according to the invention does not affect its visual transparency.

In summary, the ophthalmic devices according to the invention, such as intraocular lenses and artificial cornea or particularly contact lenses, provide a combination of low spoilation with respect to cell debris, cosmetics, tear components, lipids, proteins, salts, dust or dirt, solvent vapors or chemicals, with a high comfort for the patient wearing such opthalmic devices in view of the soft hydrogel surface which for example provides a very good on-eye movement of the ohthalmic device.

Biomedical devices such as renal dialysis membranes, blood storage bags, pacemaker leads or vascular grafts made of the composite materials of the invention resist fouling by proteins by virtue of the continuous layer of bound water, thus reducing the rate and extent of thrombosis.

Blood-contacting devices fabricated according to the present invention are therefore haemocompatible and biocompatible.

In the examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wilhelmy method using a Krüss K-12 instrument (Krüss GmbH, Hamburg, Germany). Wetting force on the solid is measured as the solid is immersed in or withdrawn from a liquid of known surface tension.

EXAMPLE A-1

Preparation of Aminofunctionalized Contact Lenses by Attaching a Bilayer a.) A 0.001 M polyacrylic acid (PM) solution ($M_n \approx 68000$) is prepared by adding 0.29 grams of a 25% aqueous PAA stock solution to 1000 ml of ultra-pure water in a beaker. Then the pH of the solution is adjusted to 2.5 by adding 1 N HCl and the solution is filtered using qualitative filter paper.

b.) A 0.001 M polyallylamine hydrochloride (PAH) solution ($M_n \approx 70000$) is prepared by adding 0.09 g PAH (solid) into a small beaker; dissolving in ultra-pure (UP) water and transfering into a 20 bigger beaker with a final volume of 1000 ml aqueous solution. The pH is then adjusted to 4.5 as measured with a pH meter. The solution is then filtered using qualitative filter paper.

c.) Swollen non-coated Lotrafilcon A lenses (polysiloxane/perfluoroalkylpolyether copolymer) in isopropanol (IPA) are individually immersed into the solution a.) for 5 minutes. After this time, the lenses are withdrawn from the solution a.) and directly immersed into the solution b.) for additional 5 minutes. No water rinse is done between these two dips. After this, the lenses are released into UP water and stored at 4° C. for further use.

EXAMPLE A-2

Preparation of Aminofunctionalized Contact Lenses by Attachment of a Bilayer a.) A 0.1% by weight solution of a branched polyacrylic acid (Carbopol® 981 NF) is prepared by adding 0.05 g of Carbopol® 981 NF (B F Goodrich) to 50 ml of isopropanol-ultra-pure water mixture (1:4) in a beaker. After complete dissolution (overnight), the pH of the solution is adjusted to 2.5 by adding 1 N HCl and the solution is filtered using qualitative filter paper.

b.) 100 ml of 0.05% solution of polyethyleneimine (PEI) is prepared by adding 0.1 g of 50% aqueous PEI stock solution into a mixture of isopropanol-ultra-pure water 1:4. The pH is then adjusted to 3.5 by adding 1 N HCl as measured by pH meter. The solution is then filtered using qualitative filter paper.

c.) Swollen non-coated Lotrafilcon A lenses in isopropanol (IPA) are individually immersed into the solution a.) for 10 minutes. The lenses are withdrawn from the solution a.) rinsed with ultra-pure water and immersed into the solution b.) for additional 10 minutes. After this, the lenses are released into ultra-pure water and stored at 4° C. for further use.

EXAMPLE B-1

Surface Binding of Reactive Photoinitiator Molecules

The aminofunctionalized contact lenses from Example A-1 are first immersed into acetonitrile for 1 hour (20 ml acetonitrile/lens). The lenses are then withdrawn and directly immersed into a 1% by weight solution of the reactive photoinitiator prepared by the addition reaction from isophorone diisocyanate and 4-(2-hydroxyethoxy) phenyl 2-hydroxy-2-propyl ketone (Darocure 2959) (synthesis see EP 0 632 329) in acetonitrile. 3 drops of triethylamine (TEA) are then added to the solution. The amino groups on the lens surface react with the isocyanato groups of the photoinitiator molecules for 12 hours. After this time, the lenses are withdrawn from the reaction solution, 3× washed and extracted in acetonitrile for 8 hours and dried under reduced pressure for 2 hours. The dried lenses are subsequently used for photografting.

EXAMPLE B-2

Surface Binding of the Reactive Photoinitiator Molecules

The aminofunctionalized contact lenses from Example A-2 are dried to the constant mass under reduced pressure. The lenses are then directly immersed into 1% by weight acetonitrile solution of the reactive photoinitiator prepared by the addition reaction from isophorone diisocyanate and 2-dimethylamino-2-benzyl-1-[4-(2-hydroxyethoxy)phenyl]-butan-1-one (synthesis see WO 96/20796(20 ml solution/lens). 3 drops of triethylamine (TEA) are then added to the solution. The amino groups on the lens surface react with the isocyanato groups of the photoinitiator molecules for 12 hours. After this time, the lenses are withdrawn from the reaction solution, 3× washed and extracted in acetonitrile for 6 hours and dried under reduced pressure for 2 hours. The dried lenses are subsequently used for photografting.

EXAMPLE C-1

Acrylamide Telomer ($M_n$ 2000) Synthesis

A 1000 mL round bottom flask is charged with a solution of 71.1 g (1 mol) Acrylamide, 4.93g (18.2 mmol) $\alpha,\alpha'$-azodiisobutyramidine dihydrochloride and 4.93 g (36.4 mmol) cysteamin-hydrochloride in 400 ml of water. The clear and slightly yellowish solution is acidified with a few drops of hydrochloric acid to pH 3. The stirred acidic solution is evacuated to 50 mbar and filled with argon. This is repeated three times. With a constant stream of Argon, this solution is poured into a 500 ml dropping funnel which is put onto an 'flow-through-reactor' consisting of an 1000ml three-necked round-bottom flask, reflux condenser, thermometer, magnetic stirrer and a 30 cm Liebig-condenser, which is filled with glass wool. The whole apparatus is constantly purged with argon. The dropping funnel is put onto the Liebig condenser, which is heated to 65° C. The flask is heated to 60° C. The solution is slowly dropped through the Liebig-condenser into the stirred flask. This takes 2.5 hrs. During this time the temperature in the flask is kept between 58–65° C. After the completed addition, the solution is stirred for 2 hrs at 60° C. NaOH is added to the clear and slightly yellowish solution until pH 10 is reached. The product is purified through reverse osmosis, using Millipore cartridge with a cut-off at 1000 Da and freeze-dried. A bright-white solid product is obtained ($NH_2$ 0.34 mEq/g, sulfur-value of the elemental analysis (0.33 mEq/g); $M_n$ 2000 g/Mol).

EXAMPLE C-2

Acrylamide Telomer ($M_n$ 1350) Synthesis

A 1000 mL round bottom flask is charged with a solution of 99.5 g (1.46 mol) acrylamide, 1.27 g (4.68 mmol)

(α,α'-azodiisobutyramidine dihydrochloride and 15.99 (0.14 mol) cysteamin-hydrochloride in 300 ml of water. The clear and slightly yellowish solution is acidified with a few drops of hydrochloric acid (32%) to pH 3. The stirred acidic solution is evacuated to 50 mbar and filled with argon. This is repeated three times. With a constant stream of argon, this solution is poured into a 500 ml dropping funnel which is put onto an 'flow-through-reactor' consisting of an 1000 ml three-necked round-bottom flask, reflux condenser, thermometer, magnetic stirrer and a 30 cm Liebig-condenser, which is filled with glass wool. The whole apparatus is constantly purged with argon. The dropping funnel is put onto the Liebig condenser, which is heated to 65° C. The flask is heated to 60° C. The solution is slowly dropped through the Liebig-condenser into the stirred flask. This takes 2 hrs. During this time the temperature in the flask is kept between 58–65° C. After the completed addition, the solution is stirred for 2 hrs at 60° C.

NaOH is added to the clear and slightly yellowish solution until pH 10 is reached. The product is purified through reverse osmosis, using Millipore cartridge with a cut-off at 1000 Da and then freeze-dried for 18 hrs. A bright-white solid product is obtained ($NH_2$ 0.70 mEq/g, sulfur-value of the elemental analysis (0.73 mEq/g; $M_n$1350 g/Mol).

EXAMPLE C-3

N,N-dimethyl Acrylamide Telomer ($M_n$1850) Synthesis

A 2000 mL round bottom flask is charged with a solution of 198.2 g (2 mol) N,N-dimethyl acrylamide, 2.72 g (10 mmol) α,α'-azodiisobutyramidine dihydrochloride and 24.8 g (0.22 mol) cysteaminhydrochloride in 600 ml of water. The clear and slightly yellowish solution is acidified with a few drops of Hydrochloric Acid (32%) to pH3. The stirred acidic solution is evacuated to 50 mbar and filled with argon. This is repeated three times. With a constant stream of argon, this solution is poured into a 1000 ml dropping funnel which is put onto an 'flow-through-reactor' consisting of an 1000 ml three-necked round-bottom flask, reflux condenser, thermometer, magnetic stirrer and a 30 cm Liebig-condenser, which is filled with glass wool. The whole apparatus is constantly purged with argon.

The dropping funnel is put onto the Liebig condenser, which is heated to 60° C. The flask is also heated to 60° C. The solution is slowly dropped through the Liebig-condenser into the stirred flask. This takes 2.5 hrs. During this time the temperature in the flask is kept between 58–65° C. After the completed addition, the solution is stirred for 2 hrs at 60° C. 30% NaOH solution is added to the clear and slightly yellowish solution until pH 10 is reached. The product is purified through reverse osmosis, using Millipore cartridge with a cut-off at 1000 Da and freeze-dried. A bright-white solid product is obtained ($NH_2$ 0.54 mEq/g; $M_n$~1850 g/Mol).

EXAMPLE D-1

Preparation of IEM-Functionalized Acrylamide Telomer Solution 7.5 g of acrylamide telomer with amino end group (amine titration=0.70 mEq/g), prepared by Example C-2 are dissolved in 80 ml of HPLC water. Argon is then let to bubble through the solution for the period of about 30 minutes. This mixture is then added to the equimolar amount (0.81 g) of isocyanatoethyl methacrylate (IEM, isocyanate titration= 6.45 mEq/g) under stirring. The whole mixture is then stirred under argon flow for 12 hours. After adding of 0.8 g of NaCl to the solution and 10 minutes stirring, the mixture is filtered through 0.45 μm Teflon filter, degassed by repeated (3×) evacuation and bubbling with argon in order to remove oxygen and used for photografting.

EXAMPLE D-2

Preparation of IEM-Functionalized N,N-dimethylacrylamide Telomer Solution 5 g of N,N-dimethylacrylamide telomer with amino end group (amine titration=0.53 mEq/g), prepared by Example C-3 are dissolved in 100 ml of HPLC water. Argon is then let to bubble through the solution for the period of about 30 minutes. This mixture is then added to the equimolar amount (0.41 g) of isocyanatoethyl methacrylate (IEM, isocyanate titration=6.45 mEq/g) under stirring. The whole mixture is then stirred under argon flow for 12 hours. After adding of 1.0 g of NaCl to the solution and 10 minutes stirring, the mixture is filtered through 0.45 μm Teflon filter, degassed with nitrogen in order to remove oxygen and used for photografting.

EXAMPLE E-1

Photografting of IEM-functionalized Acrylamide Telomers onto a Contact Lens Surface 1 ml of the IEM-functionalized acrylamide telomer solution from Example D-1 is introduced into a small Petri dish of a volume of about 2 ml in a glove box. The dried lens from Example B-1, carrying covalently linked photoinitiator molecules on its surface, is then placed into this solution and an additional 0.5 ml of the degassed solution is added on the lens in order to cover the whole lens with the solution. After 10 minutes, the Petri dish with the lens in the solution is exposed to 14.5 mW/cm$^2$ ultraviolet light for a period of about 1.5 minutes. The modified lens is then withdrawn from the solution, washed twice in destened water, continuously extracted in ultra pure water for 16 h and analyzed by AFM, ATR-FTIR and contact angle measurements.

The thickness of the coating is in the range of 250–300 nm as determined by AFM. Water/air contact angles on the modified lens are 0° adv., 0° rec., 0° hysteresis. In comparison, the contact angles of non-modified lens are 101° adv., 64° rec., 37° hysteresis. The lens held continuous water layer on the surface for over 1 minute.

EXAMPLE E-2

Photografting of IEM-Functionalized Acrylamide Telomers onto a Contact Lens Surface Two lenses from Example B-1 are coated in accordance with Example E-1, but instead of 1.5 minutes of exposition, 1.7 minutes exposition time is used for photografting. Water/air contact angles on the modified lenses are 0° adv., 0° rec., 0° hysteresis.

EXAMPLE E-3

Photografting of IEM-Functionalized N,N-dimethylacrylamide Telomers onto a Contact Lens Surface 1 ml of the IEM-functionalized N,N-dimethylacrylamide telomer solution from Example D-2 is introduced into a small Petri dish of a volume of about 2 ml in a glove box.

The dried lens from Example B-1, carrying covalently linked photoinitiator molecules on its surface, is then placed into this solution and an additional 0.5 ml of the degassed solution is added on the lens in order to cover the whole lens with the solution. After 10 minutes, the Petri dish with the lens in the solution is exposed to 14.5 mW/cm² ultraviolet light for a period of about 1.5 minutes. The lens is then turned over and the exposition is repeated by applying 14.5 mW/cm² UV light for an additional 1.5 minutes.

The modified lens is then withdrawn from the solution, washed twice in destined water, continuously extracted in ultra pure water for 16 h and analyzed by AFM, ATR-FTIR and contact angle measurements.

The thickness of the coating is in the range of 300–400 nm as determined by AFM. Water/air contact angles on the modified lens are 0° adv., 0° rec., 0° hysteresis. In comparison, the contact angles of a non-modified lens are 101° adv., 64° rec., 37° hysteresis.

EXAMPLE E-4

Photografting of IEM-Functionalized Acrylamide Telomers onto the Contact Lens Surface Under Ambient Conditions In a laminar flow hood, 1 ml of the IEM-functionalized acrylamide telomer solution from Example D-1 is introduced into a small Petri dish of a volume of about 2 ml. The dried lens from Example B-1, carrying covalently linked photoinitiator molecules on its surface, is then placed into this solution and an additional 0.5 ml of the degassed solution is added on the lens in order to cover 5 the whole lens with the solution. After 10 minutes, the Petri dish with the lens in the solution is exposed to 2.05 mW/cm² ultraviolet light (MACAM-UV-Lamp) for a period of 2.5 minutes. The modified lens is then withdrawn from the solution, washed twice in destined water, continuously extracted in ultra pure water for 16 h and analyzed by Atomic Force Microscopy (AFM), Fourier Transform Infrared-Attenuated Total Reflection Mode (ATR-FTIR) and contact angle measurements.

The thickness of the coating is in the range of 500–600 nm as determined by AFM. Water/air contact angles on the modified lens are 0° adv., 0° rec., 0° hysteresis. In comparison, the contact angles of non-modified lens are 101° adv., 64° rec., 37° hysteresis. The lens held continuous water layer on the surface for over 1 minute.

EXAMPLE E-5

Photografting of IEM-Functionalized N,N-dimethylacrylamide Telomers onto the Contact Lens Surface Under Ambient Conditions In a laminar flow hood, 1 ml of the IEM-functionalized N,N-dimethylacrylamide telomer solution from Example D-2 is introduced into a small Petri dish of a volume of about 2 ml. The dried lens from Example B-1, carrying covalently linked photoinitiator molecules on its surface, is then placed into this solution and an additional 0.5 ml of the degassed solution is added on the lens in order to cover the whole lens with the solution. After 10 minutes, the Petri dish with the lens in the solution is exposed to 2.36 mW/cm² ultraviolet light (MACAM-UV-Lamp) for a period of 2.5 minutes. The modified lens is then withdrawn from the solution, washed twice in destined water, continuously extracted in ultra pure water for 16 h and analyzed by AFM, ATR-FTIR and contact angle measurements.

Water/air contact angles on the modified lens are 6° adv., 0° rec., 6° hysteresis. In comparison, the contact angles of non-modified lens are 101° adv., 64° rec., 37° hysteresis.

EXAMPLE E-6

Photografting of IEM-Functionalized Acrylamide Telomers onto the Contact Lens Surface 1 ml of the IEM-functionalized acrylamide telomer solution from Example D-1 is introduced into a small Petri dish of a volume of about 2.5 ml in a glove box. The dried lens from Example B-2, carrying covalently linked photoinitiator molecules on its surface, is then placed into this solution and an additional 1 ml of the degassed solution is added on the lens in order to cover the whole lens with the solution. After 10 minutes, the Petri dish with the lens in the solution is exposed to 14.5 mW/cm² ultraviolet light for a period of about 3 minutes.

The modified lens is then withdrawn from the solution, washed twice in destined water, continuously extracted in ultra pure water for 16 h and analyzed by ATR-FTIR and contact angle measurements.

Water/air contact angles on the modified lens are 240 adv., 160 rec., 80 hysteresis. In comparison, the contact angles of non-modified lens are 101° adv., 64° rec., 37° hysteresis.

What is claimed is:

1. A composite material comprising (a) an inorganic or organic bulk material having attached to its surface a polyionic material that comprises covalently bound initiatior moieties for radical polymerization; and (b) a hydrophilic surface coating obtainable by applying one or more different ethylenically unsaturated hydrophilic monomers or macromonomers to the bulk material surface provided with the initiator radicals and polymerizing said monomers or macromonomers.

2. A composite material according to claim 1, wherein the composite material is a biomedical device.

3. The composite material according to claim 2, wherein the composite material is an ophthalmic device.

4. Biomedical device according to claim 3, wherein the biomedical device is a contact lens, intraocular lens or artificial cornea.

5. A composite material according to claim 1, wherein the bulk material comprises an organic polymer selected from the group consisting of a polyacrylate, a polymethacrylate, a polyacrylamide, a poly(N,N-dimethylacrylamide), a polymethacrylamide, a polyvinyl acetate, a polysiloxane, a perfluoroalkyl polyether, a poly(fluorinated acrylate), a poly(fluorinated methacrylate), and an amphiphilic segmented copolymer comprising at least one hydrophobic segment and at least one hydrophilic segment.

6. A composite material according to claim 1, wherein the polyionic material consists of one ionic polymer.

7. A composite material according to claim 1, wherein the polyionic material includes at least one bilayer, the bilayer comprising a first ionic polymer and a second ionic polymer having charges opposite of the charges of the first ionic polymer.

8. A composite material according to claim 7, wherein the bilayer(s) comprise(s) an anionic polymer selected from the group consisting of a linear polyacrylic acid, a branched polyacrylic acid, a poly-methacrylic acid, a copolymer of acrylic acid and a vinyl monomer selected from acrylamide, N,N-dimethyl acrylamide or N-vinylpyrrolidone, a copolymer of methacrylic acid and a vinyl monomer selected from acrylamide, N,N-dimethyl acrylamide or N-vinylpyrrolidone, a maleic acid homopolymer, a fumaric acid homopolymer, a copolymer of maleic or fumaric acid and a vinyl monomer selected from acrylamide, N,N-dimethyl acrylamide or N-vinylpyrrolidone, a poly(styrenesulfonic acid), a polyamido acid, a poly(2-acrylamido-2-methylpropanesulfonic acid), an alkylene polyphosphate, an alkylene polyphosphonate, a carbohydrate polyphosphate, a carbohydrate polyphosphonate; and a cationic polymer selected from the group consisting of a polyallylamine (PAH), a polyethyleneimine (PEI), a polyvinylamine homopolymer, a polyvinylamine copolymer, a poly(vinylbenzyl-tri-C1–C4-alkylammonium salt), a polymer of an aliphatic or araliphatic dihalide and an aliphatic N,N,N',N'-tetra-C1–C4-alkyl-alkylenediamine, a poly(vinylpyridin), a poly(vinylpyridinium salt), a poly (N,N-diallyl-N,N-di-C1–C4-alkyl-ammoniumhalide), a homo- or copolymer of a quaternized di-C1–C4-alkyl-aminoethyl acrylate or methacrylate, α-4-[1-tris(2-hydroxyethyl)ammonium-2-butenyl] poly[1-dimethy]ammonium-2-butenyl]-ω-tris(2-hydroxyethyl)ammonium chloride, and a polyaminoamide.

9. A composite material according to claim 7, wherein the bilayer(s) comprise(s) an anionic polymer selected from a linear polyacrylic acid, a branched polyacrylic acid or a copolymer of acrylic acid and a vinyl monomer selected from acrylamide, N,N-dimethyl acrylamide or N-vinylpyrrolidone; and a cationic polymer selected from the group consisting of a polyvinylamine homopolymer, a copolymer of vinylamine and a comonomer selected from acrylamide, methacrylamide, N,N-dimethyl acrylamide or N-vinylpyrrolidone, a polyethyleneimine homopolymer, a polyallylamine homopolymer, and a polyallylamine copolymer comprising units of allylamine and modifier units of the formula

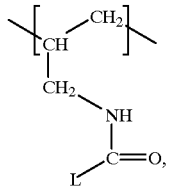

(5)

wherein L is C2–C6-alkyl which is substituted by two or more same or different substituents selected from the group consisting of hydroxy, C2–C5-alkanoyloxy and C2–C5-alkylaminocarbonyloxy.

10. A composite material according to claim 7, wherein the bilayer(s) comprise(s) a first anionic polymer and a second cationic polymer.

11. A composite material according to claim 7, wherein the bilayer(s) are formed on the bulk material surface by a dip method involving the steps of
 (i) applying a coating of a first ionic polymer to the bulk material by immersing the bulk material in a solution of the first ionic polymer; and
 (ii) applying a coating of a second ionic polymer having charges opposite of the charges of the first ionic polymer to the bulk material by immersing the bulk material in a solution of the second ionic polymer.

12. A composite material according to claim 7, wherein the bulk material comprises one or more bilayers having —$NH_2$ and/or —NH— groups attached to its surface, some of whose H atoms have been substituted by radicals of the formulae

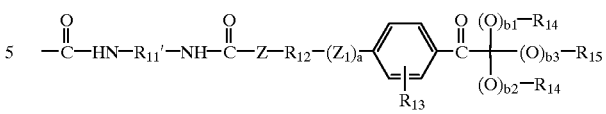

(12a)

or

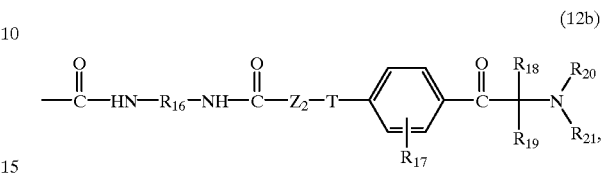

(12b)

wherein Z is bivalent —O—, —NH— or —$NR_{22}$—; $Z_1$ is —O—, —O—(O)C—, —C(O)—O— or —O—C(O)—O—; $R_{13}$ is H, $C_1$–$C_{12}$-alkyl, $C_1$–$C_{12}$-alkoxy or N-$C_1$–$C_{12}$-alkylamino; $R_{14}$ and $R_{15}$ are each independently of the other H, linear or branched $C_1$–$C_8$-alkyl, $C_1$–$C_8$-hydroxyalkyl or Cc-$C_{10}$-aryl, or the groups $R_{14}$-$(O)_{b1}$— and $R_{14}$-$(O)_{b2}$— together are —$(CH_2)_c$-wherein c is an integer from 3 to 5, or the groups $R_{14}$-$(O)_{b1}$—, $R_{14}$-$(O)_{b2}$— and $R_{15}$-$(O_1)_{b3}$— together are a radical of the formula $R_{12}$ is a direct bond or linear or branched $C_1$–$C_8$-alkylene that is unsubstituted or substituted by —OH and/or is uninterrupted or interrupted by one or more groups —O—, —O—C(O)— or —O—C(O)—O—; $R_{11}$' is branched $C_3$–$C_{18}$-alkylene, unsubstituted or $C_1$–$C_4$-alkyl- or $C_1$–$C_4$-alkoxy-substituted $C_6$–$C_{10}$-arylene, or unsubstituted or $C_1$–$C_4$-alkyl- or $C_1$–$C_4$-alkoxy-substituted $C_7$–$C_{18}$-aralkylene, unsubstituted or $C_1$–$C_4$-alkyl- or $C_1$–$C_4$-alkoxy-substituted $C_3$–$C_8$-cycloalkylene, unsubstituted or $C_1$–$C_4$-alkyl- or $C_1$–$C_4$-alkoxy-substituted $C_3$–$C_8$-cycloalkylene-$C_yH_{2y}$- or unsubstituted or $C_1$–$C_4$-alkyl- or $C_1$–$C_4$-alkoxy-substituted —$C_yH_{2y}$-$(C_3$–$C_8$-cycloalkylene)-$C_yH_{2y}$— wherein y is an integer from 1 to 6; $R_{16}$ independently has the same definitions as $R_{11}$' or is linear $C_3$–$C_{18}$-alkylene; $R_{22}$ is linear or branched $C_1$–$C_6$-alkyl; T is bivalent —O—, —NH—, —S—, $C_1$–$C_8$-alkylene or $Z_2$ is a direct bond or —O—$(CH_2)_d$— wherein d is an integer from 1 to 6 and the terminal $CH_2$ group of which is linked to the adjacent T in formula (10c); $R_{17}$ is H, $C_1$–$C_{12}$-alkyl, $C_1$–$C_{12}$-alkoxy, N—$C_1$–$C_{12}$-alkylamino or —$NR_{25}R_{26}$ wherein $R_{25}$ is $C_1$–$C_8$-alkyl and $R_{26}$ is H or $C_1$–$C_8$-alkyl; $R_{18}$ is linear or branched $C_1$–$C_8$-alkyl, $C_2$–$C_8$-alkenyl or $C_6$–$C_{10}$-aryl-$C_1$–$C_8$-alkyl; $R_{19}$ independently of $R_{18}$ has the same definitions as $R_{18}$ or is $C_6$–$C_{10}$-aryl, or $R_{18}$ and $R_{19}$ together are —$(CH_2)_e$— wherein e is an integer from 2 to 6; $R_{20}$ and $R_{20}$ are each independently of the other linear or branched $C_1$–$C_8$-alkyl that may be substituted by $C_1$–$C_4$-alkoxy, or $C_6$–$C_{10}$-aryl-$C_1$–$C_8$-alkyl or $C_2$–$C_8$-alkenyl; or $R_{20}$ and $R_{21}$ together are —$(CH_2)_{f1}$—$Z_3$—$(CH_2)_{f2}$— wherein $Z_3$ is a direct bond, —O—, —S— or —$NR_{26}$—, and $R_{26}$ is H or $C_1$–$C_8$-alkyl and f1 and f2 are each independently of the other an integer from 2 to 4; $R_{23}$ and $R_{24}$ are each independently of the other H, $C_1$–$C_8$-alkyl, $C_3$–$C_8$-cycloalkyl, benzyl or phenyl; and a, a1, b1, b2 and b3 are each independently of the other 0 or 1; subject to the provisos that b1 and b2 are each 0 when $R_{15}$ is H; that the total of (b1+b2+b3) is not exceeding 2; and that a is 0 when $R_{12}$ is a direct bond.

13. A composite material according to claim 1, wherein according to (b) a hydrophilic macromonomer of the formula

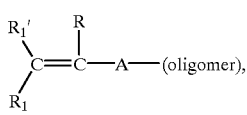 (1)

is applied, wherein $R_1$ is hydrogen, $C_1$–$C_6$-alkyl or a radical —COOR';

R, R' and $R_1'$ are each independently of the other hydrogen or $C_1$–$C_6$-alkyl;

A is a direct bond or is a radical of formula

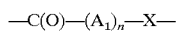 (2a)

or

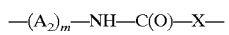 (2b);

or

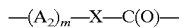 (2c);

or

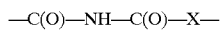 (2d);

or

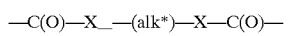 (2e);

or A and $R_1$, together with the adjacent double bond, are a radical of formula

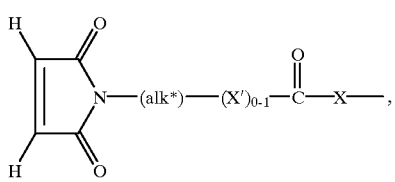 (2f)

$A_1$ is —O-$C_2$–$C_{12}$-alkylene which is unsubstituted or substituted by hydroxy, or is —O-$C_2$–$C_{12}$-alkylene—NH—C(O)— or —O-$C_2$–$C_{12}$-alkylene—O—C(O)—NH-$R_{11}$—NH—C(O)—, wherein $R_{11}$ is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$-$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene;

$A_2$ is $C_1$–$C_8$-alkylene; phenylene or benzylene;

m and n are each independently of the other the number 0 or 1;

X, $X_1$ and X' are each independently of the other a bivalent group —O— or —NR", wherein R" is hydrogen or $C_1$–$C_6$-alkyl;

(alk*) is $C_2$–$C_{12}$-alkylene; and (oligomer) denotes (i) the radical of a telomer of formula

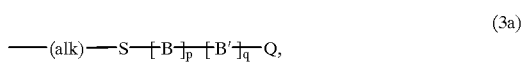 (3a)

wherein (alk) is $C_2$–$C_{12}$-alkylene,

Q is a monovalent group that is suitable to act as a polymerization chain-reaction terminator, p and q are each independently of another an integer from 0 to 250, wherein the total of (p+q) is an integer from 2 to 250, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (ii) the radical of an oligomer of the formula

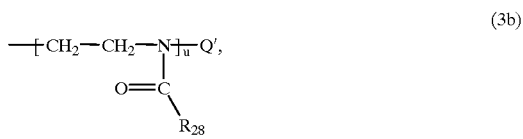 (3b)

wherein $R_{28}$ is hydrogen or unsubstituted or hydroxy-substituted $C_1$–$C_{12}$-alkyl, u is an integer from 2 to 250 and Q' is a radical of a polymerization initiator; or (iii) the radical of formula

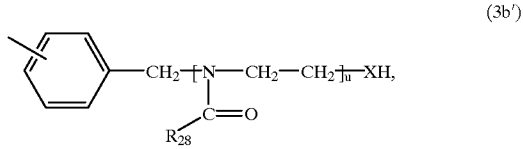 (3b')

wherein $R_{28}$, X and u are as defined above, or (iv) the radical of an oligomer of formula

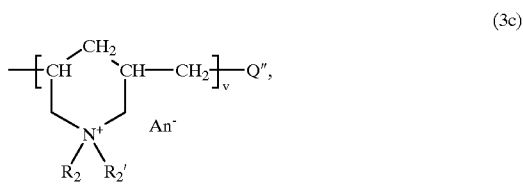 (3c)

wherein $R_2$ and $R_2'$ are each independently $C_1$–$C_4$-alkyl, An⁻ is an anion, v is an integer from 2 to 250, and Q" is a monovalent group that is suitable to act as a polymerization chain-reaction terminator; or (v) the radical of an oligopeptide of formula

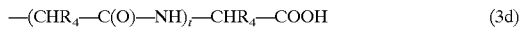  (3d)

or

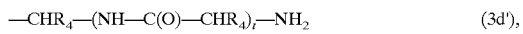  (3d'), wherein $R_4$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH$_2$ and t is an integer from 2 to 250, or the radical of an oligopeptide based on proline or hydroxyproline; or (vi) the radical of a polyalkylene oxide of formula

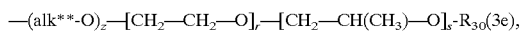

wherein $R_{30}$ is hydrogen or $C_1$–$C_{2-4}$-alkyl, (alk**) is $C_2$–$C_4$-alkylene, z is 0 or 1, r and s are each independently an integer from 0 to 250 and the total of (r+s) is from 2 to 250; or (vii) the radical of an oligosaccharide; subject to the provisos that A is not a direct bond if (oligomer) is a radical of formula (3a);

A is a direct bond if (oligomer) is a radical of formula (3b');

A is not a radical of formula (2c) or (2e) if (oligomer) is a radical of formula (3b), (3c), (3d), (3e) or is the radical of an oligosaccharide; and A is a radical of formula (2c) or (2e) if (oligomer) is a radical of formula (3d').

14. A composite material according to claim 13, wherein the hydrophilic macromonomer is a compound of formula (1), wherein R is hydrogen or methyl, $R_1$ is hydrogen, methyl or carboxyl, $R_1'$ is hydrogen, A is a radical of the formula (2a) or (2b), and (oligomer) is the radical of a telomer of formula (3a).

15. A composite material according to claim 13, wherein (oligomer) denotes a radical of formula (3a), and the radical -(alk)-S-[B]$_p$-[B']$_q$-Q is a radical of formula

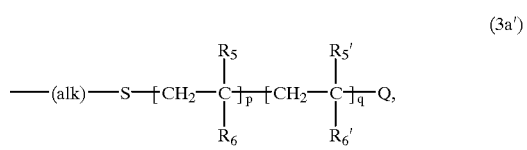  (3a')

wherein (alk) is $C_2$–$C_4$-alkylene, $R_5$ and $R_5'$ are each independently hydrogen or methyl, Q is a monovalent group that is suitable to act as a polymerization chain-reaction terminator, p and q are each independently an integer from 0 to 100 wherein the total of (p+q) is an integer from 5 to 100, and $R_6$ and $R_6'$ are each independently a radical —COOY, wherein Y is $C_1$–$C_2$-alkyl, $C_2$–$C_3$-alkyl, which is substituted by hydroxy, amino or N,N-di-$C_1$–$C_2$-alkylamino, or is a radical -$C_2$–$C_4$-alkylene—NH—C(O)—O—G wherein —O—G is the radical of trehalose; a radical —CO-NY$_1$Y$_2$, wherein Y$_1$ and Y$_2$ are each independently of the other hydrogen or $C_1$–$C_2$-alkyl which is unsubstituted or substituted by hydroxy, or Y$_1$ and Y$_2$ together with the adjacent N-atom form a N-$C_1$–$C_2$-alkylpiperazino or morpholino ring; a heterocyclic radical selected from the group consisting of N-pyrrolidonyl, 2- or 4-pyridinyl, 2-methylpyridin-5-yl, 2-, 3-oder 4-hydroxypyridinyl, N-ε-caprolactamyl, N-imidazolyl, 2-methylimidazol-1-yl, N-morpholinyl and 4—N-methylpiperazin-1-yl; —COOH; —SO$_3$H; o-, m- or p-sulfophenyl; o-, m- or p-sulfomethylphenyl; a radical —CONY$_5$Y$_6$ wherein Y$_5$ is $C_2$–$C_4$-alkyl substituted by sulfo, and Y$_6$ is hydrogen; $C_1$–$C_4$-alkyl which is substituted by —NR$_9$R$_9'$R$_9''^+$An$^-$ wherein $R_{11}$ R$_9'$ and R$_9''$ are each independently of another hydrogen or $C_1$–$C_4$-alkyl and An$^-$ is an anion; a radical —C(O)OY$_7$ wherein Y$_7$ is $C_2$–$C_4$-alkyl, which is substituted by —NR$_9$R$_9'$R$_9''^+$An$^-$ and is further unsubstituted or substituted by hydroxy, wherein R$_9$, R$_9'$, R$_9''$ and +An$^-$ are as defined; and a radical —C(O)O—CH$_2$—CH(OY$_8$)—CH$_2$—O—PO$_2^{-(CH}_2)_2$—N(CH$_3)_3^+$, wherein Y$_8$ is hydrogen or the acyl radical of a higher fatty acid.

16. A composite material according to claim 13, wherein the hydrophilic macromonomer applied according to (b) is of the formula

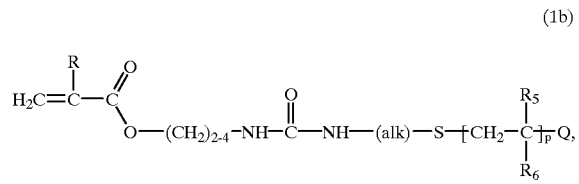  (1b)

wherein R is hydrogen or methyl, (alk) is $C_2$–$C_4$-alkylene, $R_5$ is hydrogen or methyl, p is an integer of 5 to 50, Q is as defined, and $R_6$ is a radical —CONH$_2$, —CON(CH$_3$)$_2$, —CONH—(CH$_2$)$_2$—OH,

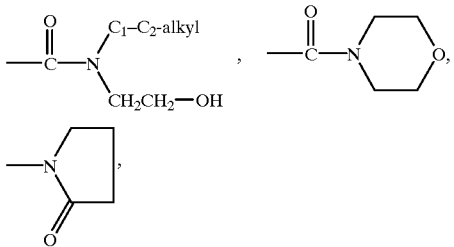

or —COO(CH$_2$)$_{2-4}$—NHC(O)—O—G wherein —O—G is the radical of trehalose.

17. A composite material according to claim 1, wherein the polymerization of the monomers or macromonomers on the modified bulk material surface is initiated by the action of irradiation.

18. A composite material according to claim 17, wherein the polymerization is initiated by the action of UV radiation for a time period of 0.5 to 5 minutes.

19. A composite material according to claim 1, wherein the hydrophilic surface coating (b) is obtainable by grafting at least one macromonomer to the bulk material surface with formation of a bottle-brush-type structure composed of tethered chains.

20. A composite material according to claim 1, wherein the hydrophilic surface coating has a coating thickness of from 0.01 to 50 μm.

21. A composite material according to claim 1, which is a contact lens, intraocular lens or artificial cornea.

22. A process for the manufacture of a composite material, which comprises the steps:

(a) providing an inorganic or organic bulk material having attached to its surface a polyionic material that comprises covalently bound initiator moieties for radical polymerization;

(b) applying a coating of one or more different ethylenically unsaturated hydrophilic monomers or macromonomers to the bulk material surface provided with the initiator radicals, and (c) polymerizing the coating of unsaturated hydrophilic macromonomers thermally or by irradiation, preferably by UV radiation.

23. A process according to claim 22, wherein the polyionic material includes at least one bilayer, the bilayer comprising a first ionic polymer and a second ionic polymer having charges opposite of the charges of the first ionic polymer, said bilayer being applied to the bulk material surface by a dip method comprising the steps of (i) immersing the bulk material in a solution of the first ionic polymer; and then (ii) immersing the bulk material in a solution of the second ionic polymer having charges opposite to the charges of the first ionic polymer.

24. A process according to claim 23, wherein the first ionic polymer is an anionic polymer comprising carboxy groups or a salt thereof, and the second ionic polymer is a cationic polymer comprising primary or secondary amino groups or a salt thereof.

25. A process according to claim 22, wherein the initiator moieties for radical polymerization are bound to the polyionic material by reaction of amino groups of the polyionic material with isocyanato groups of the initiator moiety.

26. A process according to claim 22, wherein the inorganic or organic bulk material is a contact lens, intraocular lens or artificial cornea.

* * * * *